US006852486B2

(12) United States Patent
Smith et al.

(10) Patent No.: US 6,852,486 B2
(45) Date of Patent: Feb. 8, 2005

(54) VIRAL PROTEINS CAPABLE OF BINDING LAR

(75) Inventors: Craig A. Smith, Seattle, WA (US); Raymond G. Goodwin, Seattle, WA (US)

(73) Assignee: Immunex Corp., Thousand Oaks, CA (US)

( * ) Notice: Subject to any disclaimer, the term of this patent is extended or adjusted under 35 U.S.C. 154(b) by 0 days.

(21) Appl. No.: 10/191,029

(22) Filed: Jul. 3, 2002

(65) Prior Publication Data

US 2003/0049609 A1 Mar. 13, 2003

Related U.S. Application Data

(60) Provisional application No. 60/305,223, filed on Jul. 12, 2001.

(51) Int. Cl.[7] .................................................. C12Q 1/70

(52) U.S. Cl. ........................................ 435/5; 424/232.1

(58) Field of Search ............................ 424/232.1; 435/5

(56) References Cited

U.S. PATENT DOCUMENTS 5,871,740 A 2/1999 Smith
6,355,252 B1 3/2002 Smith et al.

FOREIGN PATENT DOCUMENTS

EP 1092772 A1 4/2001
WO WO 98/37217 8/1998

OTHER PUBLICATIONS

Qiao et al., Differential Effects of Leukocyte Common Antigen–related protein, The Journal of Biological Chemistry, vol. 176, No. 12, Issue of Mar. 23, 2001, pp. 9460–9467.*

Zabolotny et al., Overexpression of the LAR (leukocyte antigen–related) protein–tyrosine phosphatase, PNAS, vol. 98, No. 9, pp. 5187–5192.*

Pickup et al., Sequence of Terminal Regions of Cowpox virus DNA, PNAS USA, vol. 79, No. 23, Dec. 1, 1982, pp. 7112–7116.*

Yang et al. Leukocyte common–antigen–related tyrosine phosphatase receptor, Carcinogenesis, 2000, col. 21, No. 2, pp. 125–131.*

Carfi, A. et al., "Structure of a soluble secreted chemokine inhibitor vCCI (p35) from cowpox virus," *PNAS 96*(*22*): 12379–12383, 1999.

Howard, S. et al., "Vaccinia virus homologues of the shope fibroma virus inverted terminal repeat proteins and a discontinuous ORF related to the tumor necrosis factor receptor family," *Virology 180*: 633–647, 1991.

Martinez–Pomares, L. et al., "Mapping and investigation of the role in pathogenesis of the major unique secreted 35–kDa protein of rabbitpox virus," *Virology 206*: 591–600, 1995.

Smith et al., "Poxvirus genomes encode a secreted, soluble protein that preferentially inhibits beta chemokine activity yet lacks sequence homology to known chemokine receptors," *Virology 236*:316–327, 1997.

* cited by examiner

*Primary Examiner*—James Housel
*Assistant Examiner*—Stacy B. Chen
(74) *Attorney, Agent, or Firm*—Patricia Anne Perkins

(57) ABSTRACT

A poxvirus protein designated A41L binds to leukocyte common-antigen-related protein (LAR). A41L is a secreted protein that can be purified from the culture supernatant of cells infected with certain poxviruses, or produced using recombinant DNA techniques. A41L polypeptides and LAR polypeptides, and nucleic acids encoding them, are provided herein. Also provided are methods of using such polypeptides and nucleic acids.

10 Claims, 2 Drawing Sheets

```
A41L_variola_Harvey           MYSLVFVILMCIPFSFQTVYD--DKSVCDSDNKEYMGIEVYVEATLDEPL  48
A41L_variola_India-1967       MYSLVFVILMCIPFSFQTVYD--DKSVCDSDNKEYMGIEVYVEATLDEPL  48
A41L_variola_Garcia-1966      MYSLVFVILMCIPFSFQTVYD--DKSVCDSDNKEYMGIEVYVEATLDEPL  48
A41L_vaccinia_WR_del          MYSLVFVILMCIPFSFQTVYD--DKSVCDSDNKEYMGIEVYVEATLDEPL  48
A41L_vaccinia_WR              MYSLVFVILMCIPFSFQTVYD--DKSVCDSDNKEYMGIEVYVEATLDEPL  48
A41L_vaccinia_Tian Tan        MYSLLFIILMCIPFSFQTVYD--DKSVCDSDNKEYMGIEVYVEATLDEPL  48
A41L_vaccinia_Ankara_.        MYSLLFIILMCIPFSFQTVYD--DKSVCDSDNKEYMGIEVYVEATLDEHL  48
A41L_vaccinia_Copenhagen      MYSLLFIILMCIPFSFQTVYD--DKSVCDSDNKEYMGIEVYVEATLDEPL  48
A41L_cowpox virus             MYSL-FIILMGLPFSFQTSEPAYDKSVCDSNNKEYMGIEVYVEATLDEPL  49

A41L_variola_Harvey           RQTTCESEIHKYGASVSNGGLNISVDLLNCFLNFHTVGVYTNRDTVYAKF  98
A41L_variola_India-1967       RQTTCESEIHKYGASVSNGGLNISVDLLNCFLNFHTVGVYTNRDTVYAKF  98
A41L_variola_Garcia-1966      RQTTCESEIHKYGASVSNGGLNISVDLLNCFLNFHTVGVYTNRDTVYAKF  98
A41L_vaccinia_WR_del          RQTTCESKIHKYGASVSNGGLNISVDLLNCFLNFHTVGVYTNRDTVYAKF  98
A41L_vaccinia_WR              RQTTCESKIHKYGASVSNGGLNISVDLLNCFLNFHTVGVYTNRDTVYAKF  98
A41L_vaccinia_Tian Tan        RQTTCESEIHKYGASVSNGGLNISVDLLNCFLNFHTVGVYTNRDTVYAKF  98
A41L_vaccinia_Ankara_.        RQTTCESEIHKYGASVSNGGLNISVDLLNCFLNFHTVGVYTNRDTVYAKF  98
A41L_vaccinia_Copenhagen      RQTTCESEIHKYGASVSNGGLNISVDLLNCFLNFHTVGVYTNRDTVYAKF  98
A41L_cowpox virus             RQTTCESEIHKYGASVSNGGLNISVDLLNCFLNFHTVGVYTNRDTVYAKF  99

A41L_variola_Harvey           ASLDPWTMEPINSMTYDDLVKLTEECIVDIYLKCEVDKTKDFIKTNGNRL 148
A41L_variola_India-1967       TSLDPWTMEPINSMTYDDLVKLTEECIVDIYLKCEVDKTKDFIKTNGNRL 148
A41L_variola_Garcia-1966      ASLDPWTMEPINSMTYDDLVKLTEECIVDIYLKCEVDKTKDFIKTNGNRL 148
A41L_vaccinia_WR_del          ASLDP--------------------------------------------- 103
A41L_vaccinia_WR              ASLDPWTTEPINSMTHDDLVKLTEECIVDIYLKCEVDKTKDFMKTNGNRL 148
A41L_vaccinia_Tian Tan        ASLDPWTTEPINSMTHDDLVKLTEECIVDIYLKCEVDKTKDFMKTNGNRL 148
A41L_vaccinia_Ankara_.        ASLDPWTTEPINSMTHDDLVKLTEECIVDIYLKCEVDKTKDFMKTNGNRL 148
A41L_vaccinia_Copenhagen      ASLDPWTTEPINSMTHDDLVKLTEECIVDIYLKCEVDKTKDFMKTNGNRL 148
A41L_cowpox virus             ASLDPST-EPINSMTHDDLVKLTEECIVDIYLKCEVDKTKDFMK-NGNRL 147
```

Figure 1A

```
A41L_variola_Harvey          KPRDFKTVPP-NVGSIIELQSDYCVNDVTAYVKIYDECGNIKQHSIPTLR 197
A41L_variola_India-1967      KPRDFKTVPP-NVGSIIELQSDYCVNDVTAYVKIYDECGNIKQHSIPTLR 197
A41L_variola_Garcia-1966     KPRDFKTVPP-NVGSIIELQSDYCVNDVTAYVKIYNECGNIKQHSIPTLR 197
A41L_vaccinia_WR_del         --------------------------------------------------
A41L_vaccinia_WR             KPRDFKTVPPSNVGSMIELQSDYCVNDVTTYVKIYDECGNIKQHSIPTLR 198
A41L_vaccinia_Tian Tan       KPRDFKTVPPSDVGSMIELQSDYCVNDVTAYVKIYDECGNIKQHSIPTLR 198
A41L_vaccinia_Ankara_.       KPRDFKTVPPSDVGSMIELQSDYCVNDVTAYVKIYDECGNIKQHSIPTLR 198
A41L_vaccinia_Copenhagen     KPRDFKTVPPSDVGSMIELQSDYCVNDVTAYVKIYDECGNIKQHSIPTLR 198
A41L_cowpox virus            KPRDFKTVPPSNVGSMIELQSDYCVEDVTAYVKIYDECGNIKQHSIPTLR 197

A41L_variola_Harvey          DYFTTTNGQPRKILKKKFDNC          218
A41L_variola_India-1967      DYFTTTNGQPRKILKKKFDNC          218
A41L_variola_Garcia-1966     DYFTTTNGQPRKILKKKFDNC          218
A41L_vaccinia_WR_del         ---------------------
A41L_vaccinia_WR             DYFTTKNGQPRKILKKKFDNC          219
A41L_vaccinia_Tian Tan       DYFTTKNGQPRKILKKKFDNC          219
A41L_vaccinia_Ankara         DYFTTKNGQPRKILKKKFDNC          219
A41L_vaccinia_Copenhagen     DYFTTKNGQPRKILKKKFDNC          219
A41L_cowpox virus            DYFTTKNGQPRKILKKKFDSC          218
```

Figure 1B

SEQUENCE LISTING

```
<160> NUMBER OF SEQ ID NOS: 13

<210> SEQ ID NO 1
<211> LENGTH: 654
<212> TYPE: DNA
<213> ORGANISM: Cowpox Virus, Strain Brighton Red
<220> FEATURE:
<221> NAME/KEY: CDS
<222> LOCATION: (1)..(654)
<223> OTHER INFORMATION:

<400> SEQUENCE: 1

atg tac tca tta ttt att att ttg atg ggt cta cca ttt agt ttt caa       48
Met Tyr Ser Leu Phe Ile Ile Leu Met Gly Leu Pro Phe Ser Phe Gln
1               5                   10                  15

aca agt gaa cca gcg tat gat aaa tcg gta tgc gat tct aac aat aaa       96
Thr Ser Glu Pro Ala Tyr Asp Lys Ser Val Cys Asp Ser Asn Asn Lys
            20                  25                  30

gaa tat atg gga ata gaa gtt tat gta gaa gca acg cta gac gaa ccc      144
Glu Tyr Met Gly Ile Glu Val Tyr Val Glu Ala Thr Leu Asp Glu Pro
        35                  40                  45

ctc aga caa aca acg tgt gaa tcc gaa atc cat aaa tat ggt gca tct      192
Leu Arg Gln Thr Thr Cys Glu Ser Glu Ile His Lys Tyr Gly Ala Ser
    50                  55                  60

gta tca aac gga gga tta aat att tct gtt gat cta tta aac tgt ttt      240
Val Ser Asn Gly Gly Leu Asn Ile Ser Val Asp Leu Leu Asn Cys Phe
65                  70                  75                  80

ctt aat ttt cat aca gtt ggt gta tac act aat cgc gat acc gta tac      288
Leu Asn Phe His Thr Val Gly Val Tyr Thr Asn Arg Asp Thr Val Tyr
                85                  90                  95

gcg aag ttt gct agt ttg gat cca tct acg gaa cct ata aat tct atg      336
Ala Lys Phe Ala Ser Leu Asp Pro Ser Thr Glu Pro Ile Asn Ser Met
            100                 105                 110

acc cat gac gat cta gta aaa tta aca gaa gaa tgt ata gtg gac att      384
Thr His Asp Asp Leu Val Lys Leu Thr Glu Glu Cys Ile Val Asp Ile
        115                 120                 125

tat tta aaa tgt gaa gtg gat aaa aca aag gat ttc atg aaa aac ggc      432
Tyr Leu Lys Cys Glu Val Asp Lys Thr Lys Asp Phe Met Lys Asn Gly
    130                 135                 140
```

-continued

```
aat aga tta aaa cca aga gac ttt aaa act gtt cct cct tct aat gta      480
Asn Arg Leu Lys Pro Arg Asp Phe Lys Thr Val Pro Pro Ser Asn Val
145                 150                 155                 160

gga agt atg atc gaa cta cag tct gac tat tgc gta gaa gat gtg act      528
Gly Ser Met Ile Glu Leu Gln Ser Asp Tyr Cys Val Glu Asp Val Thr
                165                 170                 175

gca tac gtc aaa ata tac gat gag tgc gga aac att aaa cag cat tcc      576
Ala Tyr Val Lys Ile Tyr Asp Glu Cys Gly Asn Ile Lys Gln His Ser
            180                 185                 190

att cca aca cta cga gat tat ttt acc acc aag aat ggt caa cca cgt      624
Ile Pro Thr Leu Arg Asp Tyr Phe Thr Thr Lys Asn Gly Gln Pro Arg
        195                 200                 205

aaa ata tta aag aaa aaa ttt gat agt tgt                              654
Lys Ile Leu Lys Lys Lys Phe Asp Ser Cys
    210                 215


<210> SEQ ID NO 2
<211> LENGTH: 218
<212> TYPE: PRT
<213> ORGANISM: Cowpox Virus, Strain Brighton Red

<400> SEQUENCE: 2

Met Tyr Ser Leu Phe Ile Ile Leu Met Gly Leu Pro Phe Ser Phe Gln
1               5                   10                  15

Thr Ser Glu Pro Ala Tyr Asp Lys Ser Val Cys Asp Ser Asn Asn Lys
            20                  25                  30

Glu Tyr Met Gly Ile Glu Val Tyr Val Glu Ala Thr Leu Asp Glu Pro
        35                  40                  45

Leu Arg Gln Thr Thr Cys Glu Ser Glu Ile His Lys Tyr Gly Ala Ser
    50                  55                  60

Val Ser Asn Gly Gly Leu Asn Ile Ser Val Asp Leu Leu Asn Cys Phe
65                  70                  75                  80

Leu Asn Phe His Thr Val Gly Val Tyr Thr Asn Arg Asp Thr Val Tyr
                85                  90                  95

Ala Lys Phe Ala Ser Leu Asp Pro Ser Thr Glu Pro Ile Asn Ser Met
            100                 105                 110

Thr His Asp Asp Leu Val Lys Leu Thr Glu Glu Cys Ile Val Asp Ile
        115                 120                 125

Tyr Leu Lys Cys Glu Val Asp Lys Thr Lys Asp Phe Met Lys Asn Gly
    130                 135                 140

Asn Arg Leu Lys Pro Arg Asp Phe Lys Thr Val Pro Pro Ser Asn Val
145                 150                 155                 160

Gly Ser Met Ile Glu Leu Gln Ser Asp Tyr Cys Val Glu Asp Val Thr
                165                 170                 175

Ala Tyr Val Lys Ile Tyr Asp Glu Cys Gly Asn Ile Lys Gln His Ser
            180                 185                 190

Ile Pro Thr Leu Arg Asp Tyr Phe Thr Thr Lys Asn Gly Gln Pro Arg
        195                 200                 205

Lys Ile Leu Lys Lys Lys Phe Asp Ser Cys
    210                 215


<210> SEQ ID NO 3
<211> LENGTH: 219
<212> TYPE: PRT
<213> ORGANISM: Vaccinia virus, strain Copenhagen

<400> SEQUENCE: 3
```

-continued

```
Met Tyr Ser Leu Leu Phe Ile Ile Leu Met Cys Ile Pro Phe Ser Phe
1               5                   10                  15

Gln Thr Val Tyr Asp Asp Lys Ser Val Cys Asp Ser Asp Asn Lys Glu
            20                  25                  30

Tyr Met Gly Ile Glu Val Tyr Val Glu Ala Thr Leu Asp Glu Pro Leu
        35                  40                  45

Arg Gln Thr Thr Cys Glu Ser Glu Ile His Lys Tyr Gly Ala Ser Val
    50                  55                  60

Ser Asn Gly Gly Leu Asn Ile Ser Val Asp Leu Leu Asn Cys Phe Leu
65                  70                  75                  80

Asn Phe His Thr Val Gly Val Tyr Thr Asn Arg Asp Thr Val Tyr Ala
                85                  90                  95

Lys Phe Ala Ser Leu Asp Pro Trp Thr Thr Glu Pro Ile Asn Ser Met
            100                 105                 110

Thr His Asp Asp Leu Val Lys Leu Thr Glu Glu Cys Ile Val Asp Ile
        115                 120                 125

Tyr Leu Lys Cys Glu Val Asp Lys Thr Lys Asp Phe Met Lys Thr Asn
    130                 135                 140

Gly Asn Arg Leu Lys Pro Arg Asp Phe Lys Thr Val Pro Pro Ser Asp
145                 150                 155                 160

Val Gly Ser Met Ile Glu Leu Gln Ser Asp Tyr Cys Val Asn Asp Val
                165                 170                 175

Thr Ala Tyr Val Lys Ile Tyr Asp Glu Cys Gly Asn Ile Lys Gln His
            180                 185                 190

Ser Ile Pro Thr Leu Arg Asp Tyr Phe Thr Thr Lys Asn Gly Gln Pro
        195                 200                 205

Arg Lys Ile Leu Lys Lys Lys Phe Asp Asn Cys
    210                 215


<210> SEQ ID NO 4
<211> LENGTH: 219
<212> TYPE: PRT
<213> ORGANISM: Vaccinia virus, strain Tian Tan

<400> SEQUENCE: 4

Met Tyr Ser Leu Leu Phe Ile Ile Leu Met Cys Ile Pro Phe Ser Phe
1               5                   10                  15

Gln Thr Val Tyr Asp Asp Lys Ser Val Cys Asp Ser Asp Asn Lys Glu
            20                  25                  30

Tyr Met Gly Ile Glu Val Tyr Val Glu Ala Thr Leu Asp Glu Pro Leu
        35                  40                  45

Arg Gln Thr Thr Cys Glu Ser Glu Ile His Lys Tyr Gly Ala Ser Val
    50                  55                  60

Ser Asn Gly Gly Leu Asn Ile Ser Val Asp Leu Leu Asn Cys Phe Leu
65                  70                  75                  80

Asn Phe His Thr Val Gly Val Tyr Thr Asn Arg Asp Thr Val Tyr Ala
                85                  90                  95

Lys Phe Ala Ser Leu Asp Pro Trp Thr Thr Glu Pro Ile Asn Ser Met
            100                 105                 110

Thr His Asp Asp Leu Val Lys Leu Thr Glu Glu Cys Ile Val Asp Ile
        115                 120                 125

Tyr Leu Lys Cys Glu Val Asp Lys Thr Lys Asp Phe Met Lys Thr Asn
    130                 135                 140

Gly Asn Arg Leu Lys Pro Arg Asp Phe Lys Thr Val Pro Pro Ser Asp
145                 150                 155                 160
```

-continued

```
Val Gly Ser Met Ile Glu Leu Gln Ser Asp Tyr Cys Val Asn Asp Val
                165                 170                 175

Thr Ala Tyr Val Lys Ile Tyr Asp Glu Cys Gly Asn Ile Lys Gln His
            180                 185                 190

Ser Ile Pro Thr Leu Arg Asp Tyr Phe Thr Thr Lys Asn Gly Gln Pro
        195                 200                 205

Arg Lys Ile Leu Lys Lys Lys Phe Asp Asn Cys
    210                 215


<210> SEQ ID NO 5
<211> LENGTH: 219
<212> TYPE: PRT
<213> ORGANISM: Vaccinia virus, strain Ankara

<400> SEQUENCE: 5

Met Tyr Ser Leu Leu Phe Ile Ile Leu Met Cys Ile Pro Phe Ser Phe
1               5                   10                  15

Gln Thr Val Tyr Asp Asp Lys Ser Val Cys Asp Ser Asp Asn Lys Glu
            20                  25                  30

Tyr Met Gly Ile Glu Val Tyr Val Glu Ala Thr Leu Asp Glu His Leu
        35                  40                  45

Arg Gln Thr Thr Cys Glu Ser Glu Ile His Lys Tyr Gly Ala Ser Val
    50                  55                  60

Ser Asn Gly Gly Leu Asn Ile Ser Val Asp Leu Leu Asn Cys Phe Leu
65                  70                  75                  80

Asn Phe His Thr Val Gly Val Tyr Thr Asn Arg Asp Thr Val Tyr Ala
                85                  90                  95

Lys Phe Ala Ser Leu Asp Pro Trp Thr Thr Glu Pro Ile Asn Ser Met
            100                 105                 110

Thr His Asp Asp Leu Val Lys Leu Thr Glu Glu Cys Ile Val Asp Ile
        115                 120                 125

Tyr Leu Lys Cys Glu Val Asp Lys Thr Lys Asp Phe Met Lys Thr Asn
    130                 135                 140

Gly Asn Arg Leu Lys Pro Arg Asp Phe Lys Thr Val Pro Pro Ser Asp
145                 150                 155                 160

Val Gly Ser Met Ile Glu Leu Gln Ser Asp Tyr Cys Val Asn Asp Val
                165                 170                 175

Thr Ala Tyr Val Lys Ile Tyr Asp Glu Cys Gly Asn Ile Lys Gln His
            180                 185                 190

Ser Ile Pro Thr Leu Arg Asp Tyr Phe Thr Thr Lys Asn Gly Gln Pro
        195                 200                 205

Arg Lys Ile Leu Lys Lys Lys Phe Asp Asn Cys
    210                 215


<210> SEQ ID NO 6
<211> LENGTH: 219
<212> TYPE: PRT
<213> ORGANISM: Vaccinia virus, strain WR

<400> SEQUENCE: 6

Met Tyr Ser Leu Val Phe Val Ile Leu Met Cys Ile Pro Phe Ser Phe
1               5                   10                  15

Gln Thr Val Tyr Asp Asp Lys Ser Val Cys Asp Ser Asp Asn Lys Glu
            20                  25                  30

Tyr Met Gly Ile Glu Val Tyr Val Glu Ala Thr Leu Asp Glu Pro Leu
        35                  40                  45
```

-continued

```
Arg Gln Thr Thr Cys Glu Ser Lys Ile His Lys Tyr Gly Ala Ser Val
    50                  55                  60

Ser Asn Gly Gly Leu Asn Ile Ser Val Asp Leu Leu Asn Cys Phe Leu
65                  70                  75                  80

Asn Phe His Thr Val Gly Val Tyr Thr Asn Arg Asp Thr Val Tyr Ala
                85                  90                  95

Lys Phe Ala Ser Leu Asp Pro Trp Thr Thr Glu Pro Ile Asn Ser Met
            100                 105                 110

Thr His Asp Asp Leu Val Lys Leu Thr Glu Glu Cys Ile Val Asp Ile
        115                 120                 125

Tyr Leu Lys Cys Glu Val Asp Lys Thr Lys Asp Phe Met Lys Thr Asn
    130                 135                 140

Gly Asn Arg Leu Lys Pro Arg Asp Phe Lys Thr Val Pro Pro Ser Asn
145                 150                 155                 160

Val Gly Ser Met Ile Glu Leu Gln Ser Asp Tyr Cys Val Asn Asp Val
                165                 170                 175

Thr Thr Tyr Val Lys Ile Tyr Asp Glu Cys Gly Asn Ile Lys Gln His
            180                 185                 190

Ser Ile Pro Thr Leu Arg Asp Tyr Phe Thr Thr Lys Asn Gly Gln Pro
        195                 200                 205

Arg Lys Ile Leu Lys Lys Lys Phe Asp Asn Cys
    210                 215


<210> SEQ ID NO 7
<211> LENGTH: 218
<212> TYPE: PRT
<213> ORGANISM: Variola minor virus, strain Garcia-1966

<400> SEQUENCE: 7

Met Tyr Ser Leu Val Phe Val Ile Leu Met Cys Ile Pro Phe Ser Phe
1               5                   10                  15

Gln Thr Val Tyr Asp Asp Lys Ser Val Cys Asp Ser Asp Asn Lys Glu
            20                  25                  30

Tyr Met Gly Ile Glu Val Tyr Val Glu Ala Thr Leu Asp Glu Pro Leu
        35                  40                  45

Arg Gln Thr Thr Cys Glu Ser Glu Ile His Lys Tyr Gly Ala Ser Val
    50                  55                  60

Ser Asn Gly Gly Leu Asn Ile Ser Val Asp Leu Leu Asn Cys Phe Leu
65                  70                  75                  80

Asn Phe His Thr Val Gly Val Tyr Thr Asn Arg Asp Thr Val Tyr Ala
                85                  90                  95

Lys Phe Ala Ser Leu Asp Pro Trp Thr Met Glu Pro Ile Asn Ser Met
            100                 105                 110

Thr Tyr Asp Asp Leu Val Lys Leu Thr Glu Glu Cys Ile Val Asp Ile
        115                 120                 125

Tyr Leu Lys Cys Glu Val Asp Lys Thr Lys Asp Phe Ile Lys Thr Asn
    130                 135                 140

Gly Asn Arg Leu Lys Pro Arg Asp Phe Lys Thr Val Pro Pro Asn Val
145                 150                 155                 160

Gly Ser Ile Ile Glu Leu Gln Ser Asp Tyr Cys Val Asn Asp Val Thr
                165                 170                 175

Ala Tyr Val Lys Ile Tyr Asn Glu Cys Gly Asn Ile Lys Gln His Ser
            180                 185                 190

Ile Pro Thr Leu Arg Asp Tyr Phe Thr Thr Thr Asn Gly Gln Pro Arg
```

-continued 195 200 205

Lys Ile Leu Lys Lys Lys Phe Asp Asn Cys
210 215

<210> SEQ ID NO 8
<211> LENGTH: 218
<212> TYPE: PRT
<213> ORGANISM: Variola virus, strain India-1967

<400> SEQUENCE: 8

Met Tyr Ser Leu Val Phe Val Ile Leu Met Cys Ile Pro Phe Ser Phe
1 5 10 15

Gln Thr Val Tyr Asp Asp Lys Ser Val Cys Asp Ser Asp Asn Lys Glu
20 25 30

Tyr Met Gly Ile Glu Val Tyr Val Glu Ala Thr Leu Asp Glu Pro Leu
35 40 45

Arg Gln Thr Thr Cys Glu Ser Glu Ile His Lys Tyr Gly Ala Ser Val
50 55 60

Ser Asn Gly Gly Leu Asn Ile Ser Val Asp Leu Leu Asn Cys Phe Leu
65 70 75 80

Asn Phe His Thr Val Gly Val Tyr Thr Asn Arg Asp Thr Val Tyr Ala
85 90 95

Lys Phe Thr Ser Leu Asp Pro Trp Thr Met Glu Pro Ile Asn Ser Met
100 105 110

Thr Tyr Asp Asp Leu Val Lys Leu Thr Glu Glu Cys Ile Val Asp Ile
115 120 125

Tyr Leu Lys Cys Glu Val Asp Lys Thr Lys Asp Phe Ile Lys Thr Asn
130 135 140

Gly Asn Arg Leu Lys Pro Arg Asp Phe Lys Thr Val Pro Pro Asn Val
145 150 155 160

Gly Ser Ile Ile Glu Leu Gln Ser Asp Tyr Cys Val Asn Asp Val Thr
165 170 175

Ala Tyr Val Lys Ile Tyr Asp Glu Cys Gly Asn Ile Lys Gln His Ser
180 185 190

Ile Pro Thr Leu Arg Asp Tyr Phe Thr Thr Thr Asn Gly Gln Pro Arg
195 200 205

Lys Ile Leu Lys Lys Lys Phe Asp Asn Cys
210 215

<210> SEQ ID NO 9
<211> LENGTH: 218
<212> TYPE: PRT
<213> ORGANISM: Variola major virus, strain Harvey

<400> SEQUENCE: 9

Met Tyr Ser Leu Val Phe Val Ile Leu Met Cys Ile Pro Phe Ser Phe
1 5 10 15

Gln Thr Val Tyr Asp Asp Lys Ser Val Cys Asp Ser Asp Asn Lys Glu
20 25 30

Tyr Met Gly Ile Glu Val Tyr Val Glu Ala Thr Leu Asp Glu Pro Leu
35 40 45

Arg Gln Thr Thr Cys Glu Ser Glu Ile His Lys Tyr Gly Ala Ser Val
50 55 60

Ser Asn Gly Gly Leu Asn Ile Ser Val Asp Leu Leu Asn Cys Phe Leu
65 70 75 80

Asn Phe His Thr Val Gly Val Tyr Thr Asn Arg Asp Thr Val Tyr Ala

-continued

```
                85                  90                  95

Lys Phe Ala Ser Leu Asp Pro Trp Thr Met Glu Pro Ile Asn Ser Met
            100                 105                 110

Thr Tyr Asp Asp Leu Val Lys Leu Thr Glu Glu Cys Ile Val Asp Ile
        115                 120                 125

Tyr Leu Lys Cys Glu Val Asp Lys Thr Lys Asp Phe Ile Lys Thr Asn
    130                 135                 140

Gly Asn Arg Leu Lys Pro Arg Asp Phe Lys Thr Val Pro Pro Asn Val
145                 150                 155                 160

Gly Ser Ile Ile Glu Leu Gln Ser Asp Tyr Cys Val Asn Asp Val Thr
                165                 170                 175

Ala Tyr Val Lys Ile Tyr Asp Glu Cys Gly Asn Ile Lys Gln His Ser
            180                 185                 190

Ile Pro Thr Leu Arg Asp Tyr Phe Thr Thr Thr Asn Gly Gln Pro Arg
        195                 200                 205

Lys Ile Leu Lys Lys Lys Phe Asp Asn Cys
    210                 215
```

<210> SEQ ID NO 10
<211> LENGTH: 1194
<212> TYPE: PRT
<213> ORGANISM: Homo sapiens

<400> SEQUENCE: 10

```
Met Val Pro Leu Val Pro Ala Leu Val Met Leu Gly Leu Val Ala Gly
1               5                   10                  15

Ala His Gly Asp Ser Lys Pro Val Phe Ile Lys Val Pro Glu Asp Gln
            20                  25                  30

Thr Gly Leu Ser Gly Gly Val Ala Ser Phe Val Cys Gln Ala Thr Gly
        35                  40                  45

Glu Pro Lys Pro Arg Ile Thr Trp Met Lys Lys Gly Lys Lys Val Ser
    50                  55                  60

Ser Gln Arg Phe Glu Val Ile Glu Phe Asp Asp Gly Ala Gly Ser Val
65                  70                  75                  80

Leu Arg Ile Gln Pro Leu Arg Val Gln Arg Asp Glu Ala Ile Tyr Glu
                85                  90                  95

Cys Thr Ala Thr Asn Ser Leu Gly Glu Ile Asn Thr Ser Ala Lys Leu
            100                 105                 110

Ser Val Leu Glu Glu Glu Gln Leu Pro Pro Gly Phe Pro Ser Ile Asp
        115                 120                 125

Met Gly Pro Gln Leu Lys Val Val Glu Lys Ala Arg Thr Ala Thr Met
    130                 135                 140

Leu Cys Ala Ala Gly Gly Asn Pro Asp Pro Glu Ile Ser Trp Phe Lys
145                 150                 155                 160

Asp Phe Leu Pro Val Asp Pro Ala Thr Ser Asn Gly Arg Ile Lys Gln
                165                 170                 175

Leu Arg Ser Gly Gly Ser Pro Ile Arg Gly Ala Leu Gln Ile Glu Ser
            180                 185                 190

Ser Glu Glu Ser Asp Gln Gly Lys Tyr Glu Cys Val Ala Thr Asn Ser
        195                 200                 205

Ala Gly Thr Arg Tyr Ser Ala Pro Ala Asn Leu Tyr Val Arg Val Arg
    210                 215                 220

Arg Val Ala Pro Arg Phe Ser Ile Pro Pro Ser Ser Gln Glu Val Met
225                 230                 235                 240
```

-continued

```
Pro Gly Gly Ser Val Asn Leu Thr Cys Val Ala Val Gly Ala Pro Met
                245                 250                 255

Pro Tyr Val Lys Trp Met Met Gly Ala Glu Glu Leu Thr Lys Glu Asp
            260                 265                 270

Glu Met Pro Val Gly Arg Asn Val Leu Glu Leu Ser Asn Val Val Arg
        275                 280                 285

Ser Ala Asn Tyr Thr Cys Val Ala Ile Ser Ser Leu Gly Met Ile Glu
    290                 295                 300

Ala Thr Ala Gln Val Thr Val Lys Ala Leu Pro Lys Pro Pro Ile Asp
305                 310                 315                 320

Leu Val Val Thr Glu Thr Thr Ala Thr Ser Val Thr Leu Thr Trp Asp
                325                 330                 335

Ser Gly Asn Ser Glu Pro Val Thr Tyr Tyr Gly Ile Gln Tyr Arg Ala
            340                 345                 350

Ala Gly Thr Glu Gly Pro Phe Gln Glu Val Asp Gly Val Ala Thr Thr
        355                 360                 365

Arg Tyr Ser Ile Gly Gly Leu Ser Pro Phe Ser Glu Tyr Ala Phe Arg
    370                 375                 380

Val Leu Ala Val Asn Ser Ile Gly Arg Gly Pro Pro Ser Glu Ala Val
385                 390                 395                 400

Arg Ala Arg Thr Gly Glu Gln Ala Pro Ser Ser Pro Pro Arg Arg Val
                405                 410                 415

Gln Ala Arg Met Leu Ser Ala Ser Thr Met Leu Val Gln Trp Glu Pro
            420                 425                 430

Pro Glu Glu Pro Asn Gly Leu Val Arg Gly Tyr Arg Val Tyr Tyr Thr
        435                 440                 445

Pro Asp Ser Arg Arg Pro Pro Asn Ala Trp His Lys His Asn Thr Asp
    450                 455                 460

Ala Gly Leu Leu Thr Thr Val Gly Ser Leu Leu Pro Gly Ile Thr Tyr
465                 470                 475                 480

Ser Leu Arg Val Leu Ala Phe Thr Ala Val Gly Asp Gly Pro Pro Ser
                485                 490                 495

Pro Thr Ile Gln Val Lys Thr Gln Gln Gly Val Pro Ala Gln Pro Ala
            500                 505                 510

Asp Phe Gln Ala Glu Val Glu Ser Asp Thr Arg Ile Gln Leu Ser Trp
        515                 520                 525

Leu Leu Pro Pro Gln Glu Arg Ile Ile Met Tyr Glu Leu Val Tyr Trp
    530                 535                 540

Ala Ala Glu Asp Glu Asp Gln Gln His Lys Val Thr Phe Asp Pro Thr
545                 550                 555                 560

Ser Ser Tyr Thr Leu Glu Asp Leu Lys Pro Asp Thr Leu Tyr Arg Phe
                565                 570                 575

Gln Leu Ala Ala Arg Ser Asp Met Gly Val Gly Val Phe Thr Pro Thr
            580                 585                 590

Ile Glu Ala Arg Thr Ala Gln Ser Met Pro Ser Gly Pro Pro Arg Lys
        595                 600                 605

Val Glu Val Glu Pro Leu Asn Ser Thr Ala Val His Val Tyr Trp Lys
    610                 615                 620

Leu Pro Val Pro Ser Lys Gln His Gly Gln Ile Arg Gly Tyr Gln Val
625                 630                 635                 640

Thr Tyr Val Arg Leu Glu Asn Gly Glu Pro Arg Gly Leu Pro Ile Ile
                645                 650                 655

Gln Asp Val Met Leu Ala Glu Ala Gln Trp Arg Pro Glu Glu Ser Glu
```

-continued

```
            660                 665                 670

Asp Tyr Glu Thr Thr Ile Ser Gly Leu Thr Pro Glu Thr Thr Tyr Ser
        675                 680                 685

Val Thr Val Ala Ala Tyr Thr Thr Lys Gly Asp Gly Ala Arg Ser Lys
    690                 695                 700

Pro Lys Ile Val Thr Thr Thr Gly Ala Val Phe Ala Lys Asn Phe Arg
705                 710                 715                 720

Val Ala Ala Ala Met Lys Thr Ser Val Leu Leu Ser Trp Glu Val Pro
                725                 730                 735

Asp Ser Tyr Lys Ser Ala Val Pro Phe Lys Ile Leu Tyr Asn Gly Gln
            740                 745                 750

Ser Val Glu Val Asp Gly His Ser Met Arg Lys Leu Ile Ala Asp Leu
        755                 760                 765

Gln Pro Asn Thr Glu Tyr Ser Phe Val Leu Met Asn Arg Gly Ser Ser
    770                 775                 780

Ala Gly Gly Leu Gln His Leu Val Ser Ile Arg Thr Ala Pro Asp Leu
785                 790                 795                 800

Leu Pro His Lys Pro Leu Pro Ala Ser Ala Tyr Ile Glu Asp Gly Arg
                805                 810                 815

Phe Asp Leu Ser Met Pro His Val Gln Asp Pro Ser Leu Val Arg Trp
            820                 825                 830

Phe Tyr Ile Val Val Val Pro Ile Asp Arg Val Gly Gly Ser Met Leu
        835                 840                 845

Thr Pro Arg Trp Ser Thr Pro Glu Glu Leu Glu Leu Asp Glu Leu Leu
    850                 855                 860

Glu Ala Ile Glu Gln Gly Gly Glu Glu Gln Arg Arg Arg Arg Arg Gln
865                 870                 875                 880

Ala Glu Arg Leu Lys Pro Tyr Val Ala Ala Gln Leu Asp Val Leu Pro
                885                 890                 895

Glu Thr Phe Thr Leu Gly Asp Lys Lys Asn Tyr Arg Gly Phe Tyr Asn
            900                 905                 910

Arg Pro Leu Ser Pro Asp Leu Ser Tyr Gln Cys Phe Val Leu Ala Ser
        915                 920                 925

Leu Lys Glu Pro Met Asp Gln Lys Arg Tyr Ala Ser Ser Pro Tyr Ser
    930                 935                 940

Asp Glu Ile Val Val Gln Val Thr Pro Ala Gln Gln Gln Glu Glu Pro
945                 950                 955                 960

Glu Met Leu Trp Arg Ser Cys Asp Lys Thr His Thr Cys Pro Pro Cys
                965                 970                 975

Pro Ala Pro Glu Ala Glu Gly Ala Pro Ser Val Phe Leu Phe Pro Pro
            980                 985                 990

Lys Pro Lys Asp Thr Leu Met Ile  Ser Arg Thr Pro Glu  Val Thr Cys
        995                 1000                1005

Val Val  Val Asp Val Ser His  Glu Asp Pro Glu Val  Lys Phe Asn
    1010                1015                1020

Trp Tyr  Val Asp Gly Val Glu  Val His Asn Ala Lys  Thr Lys Pro
    1025                1030                1035

Arg Glu  Glu Gln Tyr Asn Ser  Thr Tyr Arg Val Val  Ser Val Leu
    1040                1045                1050

Thr Val  Leu His Gln Asp Trp  Leu Asn Gly Lys Glu  Tyr Lys Cys
    1055                1060                1065

Lys Val  Ser Asn Lys Ala Leu  Pro Ala Pro Ile Glu  Lys Thr Ile
    1070                1075                1080
```

-continued

```
Ser Lys  Ala Lys Gly Gln Pro  Arg Glu Pro Gln Val  Tyr Thr Leu
    1085                 1090                 1095

Pro Pro  Ser Arg Glu Glu Met  Thr Lys Asn Gln Val  Ser Leu Thr
    1100                 1105                 1110

Cys Leu  Val Lys Gly Phe Tyr  Pro Ser Asp Ile Ala  Val Glu Trp
    1115                 1120                 1125

Glu Ser  Asn Gly Gln Pro Glu  Asn Asn Tyr Lys Thr  Thr Pro Pro
    1130                 1135                 1140

Val Leu  Asp Ser Asp Gly Ser  Phe Phe Leu Tyr Ser  Lys Leu Thr
    1145                 1150                 1155

Val Asp  Lys Ser Arg Trp Gln  Gln Gly Asn Val Phe  Ser Cys Ser
    1160                 1165                 1170

Val Met  His Glu Ala Leu His  Asn His Tyr Thr Gln  Lys Ser Leu
    1175                 1180                 1185

Ser Leu  Ser Pro Gly Lys
    1190


<210> SEQ ID NO 11
<211> LENGTH: 8
<212> TYPE: PRT
<213> ORGANISM: Artificial Sequence
<220> FEATURE:
<223> OTHER INFORMATION: FLAG Peptide

<400> SEQUENCE: 11

Asp Tyr Lys Asp Asp Asp Asp Lys
1               5


<210> SEQ ID NO 12
<211> LENGTH: 306
<212> TYPE: PRT
<213> ORGANISM: Homo sapiens

<400> SEQUENCE: 12

Met Val Pro Leu Val Pro Ala Leu Val Met Leu Gly Leu Val Ala Gly
1               5                   10                  15

Ala His Gly Asp Ser Lys Pro Val Phe Ile Lys Val Pro Glu Asp Gln
            20                  25                  30

Thr Gly Leu Ser Gly Gly Val Ala Ser Phe Val Cys Gln Ala Thr Gly
        35                  40                  45

Glu Pro Lys Pro Arg Ile Thr Trp Met Lys Lys Gly Lys Lys Val Ser
    50                  55                  60

Ser Gln Arg Phe Glu Val Ile Glu Phe Asp Asp Gly Ala Gly Ser Val
65                  70                  75                  80

Leu Arg Ile Gln Pro Leu Arg Val Gln Arg Asp Glu Ala Ile Tyr Glu
                85                  90                  95

Cys Thr Ala Thr Asn Ser Leu Gly Glu Ile Asn Thr Ser Ala Lys Leu
            100                 105                 110

Ser Val Leu Glu Glu Glu Gln Leu Pro Pro Gly Phe Pro Ser Ile Asp
        115                 120                 125

Met Gly Pro Gln Leu Lys Val Val Glu Lys Ala Arg Thr Ala Thr Met
    130                 135                 140

Leu Cys Ala Ala Gly Gly Asn Pro Asp Pro Glu Ile Ser Trp Phe Lys
145                 150                 155                 160

Asp Phe Leu Pro Val Asp Pro Ala Thr Ser Asn Gly Arg Ile Lys Gln
                165                 170                 175
```

-continued

```
Leu Arg Ser Gly Ala Leu Gln Ile Glu Ser Ser Glu Glu Ser Asp Gln
            180                 185                 190

Gly Lys Tyr Glu Cys Val Ala Thr Asn Ser Ala Gly Thr Arg Tyr Ser
        195                 200                 205

Ala Pro Ala Asn Leu Tyr Val Arg Val Arg Arg Val Ala Pro Arg Phe
    210                 215                 220

Ser Ile Pro Pro Ser Ser Gln Glu Val Met Pro Gly Gly Ser Val Asn
225                 230                 235                 240

Leu Thr Cys Val Ala Val Gly Ala Pro Met Pro Tyr Val Lys Trp Met
                245                 250                 255

Met Gly Ala Glu Glu Leu Thr Lys Glu Asp Glu Met Pro Val Gly Arg
            260                 265                 270

Asn Val Leu Glu Leu Ser Asn Val Val Arg Ser Ala Asn Tyr Thr Cys
        275                 280                 285

Val Ala Ile Ser Ser Leu Gly Met Ile Glu Ala Thr Ala Gln Val Thr
    290                 295                 300

Val Lys
305


<210> SEQ ID NO 13
<211> LENGTH: 18
<212> TYPE: DNA
<213> ORGANISM: Homo sapiens

<400> SEQUENCE: 13

ggttcaccaa tcagaggt                                                 18
```

VIRAL PROTEINS CAPABLE OF BINDING LAR

This application claims priority from provisional application No. 60/305,223 filed Jul. 12, 2001.

BACKGROUND OF THE INVENTION

Poxviruses form a group of large, double-stranded DNA viruses that have adapted to replicate in numerous hosts. One adaptive mechanism that many poxviruses have utilized is the acquisition of host genes that allow the viruses to evade the host's immune system and/or facilitate viral replication (Bugert and Darai, *Virus Genes* 21:111, 2000; Alcami et al., *Semin. Virol.* 8:419, 1998; McFadden and Barry, *Semin. Virol.* 8:429, 1998). This process has been facilitated by the relatively large size and complexity of the poxvirus genome; vaccinia virus, a prototype poxvirus widely used as a smallpox vaccine, has a genome of approximately 190 Kbp that could potentially encode more than 200 proteins (Goebel et al., *Virology* 179:247, 1990). Despite the fact that the entire genome of vaccinia virus has been sequenced, the function of many of the potential open reading frames (ORFs), and the existence of polypeptides encoded thereby, remains unknown.

A41L is an ORF present in several different poxviruses, including Cowpox virus (CPV), vaccinia virus (strains Copenhagen, Ankara, Tian Tan and WR) and variola virus (including strains Harvey, India-1967 and Garcia-1966). An ORF from vaccinia strain WR referred to as SalF4L in Howard et al., *Virology* 180:633, 1991, was noted to exhibit week similarity with an ORF from Shope fibroma virus (SFV) referred to therein as T1. The protein encoded by the SFV T1 ORF is referred to as p35 in Martinez-Pomarres et al. (*Virology* 206:591, 1995), who state that SaTF4L did not exhibit significant homology with p35, p35 binds to, and inhibits the activity of, certain chemokines (Smith et al., *Virology* 236:316, 1997; U.S. Pat. No. 5,871,740). An A41L protein made by recombinant baculovirus expression was reported to specifically bind the chemokines Mig and IP-10, but not other chemokines, by Smith et al. in WO98/37217.

The leukocyte common-antigen-related protein (LAR) is a prototypic member of the superfamily of receptor-like protein tyrosine phosphatases (PTPs) with immunoglobulin and fibronection type III-like motifs in the extracellular domain (Streuli et al., *J. Exp. Med.* 168:1523, 1988). Several alternatively spliced variants of LAR have been identified, and are believed to be developmentally regulated (O'Grady et al., *J. Biol. Chem.* 269:25193, 1994; Zhang and Longo, *J. Cell. Biol.* 128:415, 1995; Honkaniemi et al., *Mol. Brain. Res.* 61:1, 1998). In humans, the LAR gene maps to chromosome 1p32, a region that is frequently deleted in tumors of neuroectodermal origin (Jirik et al., *Cytogenet. Cell Genet.* 61:266, 1992).

Changes in LAR expression and splicing have been associated with changes in the ability of cells to proliferate (Yang et al., *Carcinogenesis* 21:125; Tisi et al., *J. Neurobiol.* 42:477, 2000). Transfection of a human breast carcinoma cell line that overexpresses the protein tyrosine kinase $p185^{neu}$ with cDNA for LAR resulted in suppression of tumor cell growth (Zhai et al., *Mol. Carcinogen.* 14:103, 1995), suggesting a role for LAR as a tumor suppressor. The related PTP, CD45, suppresses Janus kinase (JAK) kinases and negatively regulates cytokine receptor signaling; LAR also dephosphorylates JAK2 (Irie-Sasaki et al., *Nature* 409:349, 2001). LAR has also been found to associate with the insulin receptor, and play a role in glucose homeostasis (Ahmad and Goldstein, *J. Biol. Chem.* 272:448, 1997; Ren et al., *Diabetes* 47:493, 1998). These and other functional roles of LAR are discussed in EP 1 092 772 (Yamamoto et al.; 2001).

Heretofore, the function of any peptide encoded by an A41L ORF was unclear. Moreover, despite a role being known for LAR in glucose metabolism and/or cell replication, it was previously unknown whether LAR plays a role in an immune or inflammatory response, or what such role might be. Accordingly, there is a need in the art to determine the biologic function(s) of a protein or proteins encoded by an A41L ORF, and to determine the role of LAR in an immune or inflammatory response.

SUMMARY OF THE INVENTION

The present invention provides a protein designated A41L that is capable of binding to leukocyte common-antigen-related protein (LAR), a protein tyrosine phosphatase (PTPase). A method for treating a disorder mediated by LAR involves administering an effective amount of a LAR agonist or antagonist to a mammal afflicted with such a disorder. Preferably the biological activity of LAR that is regulated is its ability to dephosphorylate specific proteins (for example, JAKs).

Isolated nucleic acids encoding A41L are also provided herein, along with expression vectors comprising the A41L DNA. Methods for producing recombinant A41L polypeptides involve culturing host cells containing the expression vectors under conditions appropriate for expression of A41L, and recovering the expressed A41L from the cell culture. Certain embodiments of the invention are directed to A41L DNA derived from cowpox virus, the A41L protein encoded thereby, and uses thereof.

The present invention also provides methods for screening for a molecule that alters (antagonizes or agonizes) an activity of LAR. In one aspect, the inventive methods utilize homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence. In another aspect, the inventive methods utilize heterogeneous assay formats such as enzyme-linked immunosorbant assays (ELISA) or radioimmunoassays. In yet another aspect of the invention are cell-based assays, for example those utilizing reporter genes, as well as functional assays that analyze the effect of an antagonist or agonist on biological function(s).

The invention further provides methods for producing information comprising the identity of a compound that alters one or more biological activities of LAR, the method comprising using assay methods of the invention to identify one or more compounds that alter the binding of A41L and LAR. In one preferred embodiment, the compound decreases (or antagonizes) the binding of A41L and LAR, and in another distinct embodiment, the compound increases (or agonizes) the binding of A41L and LAR.

Also provided by the invention is the information produced according to the inventive methods, said information comprising the identity of a compound that alters the biological activity of LAR, and preferably embodied in a storage medium selected from the group consisting of paper, magnetic tape, optical tape, floppy disks, compact disks, computer system hard drives, and computer memory units. In a further aspect, the invention provides a database comprising said information, wherein the information is preferably embodied in a computer-readable medium, and a separate embodiment wherein the information is embodied in a human-readable medium.

Additionally provided by the invention is a computer system comprising a database containing records pertaining to a plurality of compounds, wherein the records comprise results of an assay of the invention, and a user interface allowing a user to access information regarding the plurality of compounds. In another aspect of the invention, a computer system is provided for storing and retrieving data on a plurality of compounds, the computer system comprising: (a) input means for entering data for the compounds into a storage medium; (b) a processor for creating an individual record for each compound, the processor assigning specific identifying values for each compound; (c) means for selecting one or more of the records based on results in an assay; and (d) means for transmitting information in the record or records to an output device to produce a report; preferably a report in human-readable form, and wherein the computer system preferably further comprises a video display unit.

The invention also provides a method of using the computer system of the invention to select one or more compounds for testing from a plurality of compounds having records stored in a database, the method comprising: displaying a list of said records or a field for entering information identifying one or more of said records; and selecting one or more of the records from the list or the record or records identified by entering information in the field. Further, the invention provides a method of operating a computer system for analyzing compounds that modulate the interaction of A41L and LAR, the method comprising: (a) entering data relating to a plurality of compounds into a storage medium; (b) processing the data to create an individual record for each compound; (c) testing compounds for the ability to modulate binding of A41L to LAR; and (d) communicating results from the testing into the storage medium such that results for each compound are associated with the individual record for that compound; wherein in one embodiment the storage medium comprises one or more computer memory units, and in another embodiment the computer system further comprises a video display unit.

In yet another aspect of the invention, a database is provided comprising records generated according to the methods of the invention, and a method is provided for selecting compounds that modulate the interaction of A41L and LAR, comprising compiling said database, analyzing the testing results, and selecting one or more compounds.

Candidate molecules that are determined to alter an activity of LAR are useful, for example, for the further definition of LAR-mediated signaling pathways, and for the manipulation of LAR-mediated cellular responses. Moreover, LAR signaling agonists and antagonists provide therapeutic agents for an immune and/or inflammatory response.

BRIEF DESCRIPTION OF THE DRAWINGS

FIG. 1 depicts an alignment of several members of the A41L gene family. Conserved cysteines are shown in bold face type.

DETAILED DESCRIPTION OF THE INVENTION

The ability of a protein designated A41L to bind LAR is disclosed herein. A41L is encoded by an open reading frame (ORF) present in several different poxviruses. The present invention provides a method for modulating a biological activity of LAR by contacting a cell expressing LAR with an agonist or antagonist of LAR. A disorder mediated by LAR is treated by administering an effective amount of an agonist or antagonist of LAR to a mammal afflicted with such a disorder.

The present invention provides purified A41L polypeptides and pharmaceutical compositions containing such polypeptides. Isolated nucleic acids encoding A41L are provided herein, along with expression vectors comprising the A41L nucleic acid. Methods for producing recombinant A41L polypeptides involve culturing host cells containing the expression vectors under conditions appropriate for expression of A41L, and recovering the expressed A41L from the cell culture. Certain embodiments of the invention are directed to A41L nucleic acids and polypeptides, and uses thereof.

As used herein, A41L polypeptide refers to a group of secreted, soluble polypeptides that are poxvirus virulence factors and encoded in a number of poxvirus genomes, including, but not limited to, variola, cowpox, vaccinia, myxoma, and Shope fribroma viruses. The A41L polypeptides are capable of specifically binding known LAR. A number of A41L polypeptides and their amino acid sequences are shown in FIG. 1. References to A41L polypeptides herein additionally encompass variants of A41L polypeptides, as described herein.

A DNA and encoded amino acid sequence for cowpox A41L is presented in SEQ ID NO:1 and SEQ ID NO:2, respectively. Another A41L protein suitable for use in the present invention is encoded by an open reading frame in the genome of the Copenhagen strain of vaccinia virus. The DNA sequence of the genome for this strain of vaccinia virus is known; the amino acid sequence of a putative A41L ORF is presented herein in SEQ ID NO:3. The cowpox A41L amino acid sequence in SEQ ID NO:2 is 93% identical to the vaccinia virus A41L amino acid sequence presented in SEQ ID NO:3. Additional strains of vaccinia virus also include putative ORFs corresponding to A41L; these include strain Tian Tan (SEQ ID NO:4), strain Ankara (SEQ ID NO:5), and strain WR (SEQ ID NO:6; a deleted form of this ORF has also been reported in Blasco et al. (*J. Virol.* 65:4598, 1991) and is shown in FIG. 1.

Another suitable A41L protein is encoded by an open reading frame in the genome of several strains of variola (smallpox) virus. A putative A41L protein from variola minor virus, strain Garcia-1966 is presented in SEQ ID NO:7; a putative A41L protein from variola virus, strain India-1967 is shown in SEQ ID NO:8; and ; a putative A41L protein from variola major virus, strain Harvey is shown in SEQ ID NO:9. The amino acid sequence shown in SEQ ID NO:8 is 90% identical to that of the cowpox A41L of SEQ ID NO:2.

Homologs of certain viral proteins have been isolated from mammalian cell sources. Thus, the present invention encompasses homologs of the viral A41L proteins, wherein the homologs are derived from higher organisms, including mammalian cells. Cowpox A41L DNA may be radiolabeled and used as a probe in cross-species hybridization procedures, to detect A41L DNAs in the genomes of other virus strains, or in nucleic acids derived from cells of higher organisms. Alternatively, the nucleotide and/or amino acid sequences in various databases can be examined for homology to A41L proteins, and homologous mammalian (or other species) proteins and the DNAs encoding them identified and isolated.

The above-described A41L proteins comprise a hydrophobic region at the N-terminus of the protein that is believed to function as a signal peptide. The signal peptide is predicted to be cleaved after amino acid 19 of SEQ ID NO:2 (which corresponds to amino acid 20 of SEQ ID NOs:3 through 9). Thus, mature A41L proteins include those comprising amino acids 20 through 218 of SEQ ID NO:2, amino acids 21 through 219 of SEQ ID NOs:3, 4, 5, and 6, and amino acids 21 through 218 of SEQ ID NOs:7, 8, and 9.

Additionally, N-terminal amino acid sequencing of purified CPV A41L demonstrated that the N-terminal amino acid residue is the Thr at amino acid number 17 of SEQ ID NO:2 (which corresponds to amino acid number 18 of SEQ ID NOs:3 through 9). Accordingly, mature A41L proteins also include those comprising amino acids 17 through 218 of SEQ ID NO:2, amino acids 18 through 219 of SEQ ID NOs:3, 4, 5, and 6, and amino acids 18 through 218 of SEQ ID NOs:7, 8, and 9.

Regarding the foregoing discussion of signal peptides and mature A41L protein, the skilled artisan will recognize that the above-described boundaries of such regions of the protein are approximate. For example, although computer programs that predict the site of cleavage of a signal peptide are available, cleavage can occur at sites other than those predicted. Further, it is recognized that a protein preparation can comprise a mixture of protein molecules having different N-terminal amino acids, due to cleavage of the signal peptide at more than one site. In addition, post-translational processing can vary according to the particular expression system employed. Thus, the N- or C-terminal amino acid of a mature recombinant protein may vary according to the type of host cells in which the protein was expressed, for example.

The invention further provides various forms of cowpox A41L proteins, including a protein comprising amino acids x to y of SEQ ID NO:2, wherein x represents an integer from 1 to 25, inclusive, and y represents an integer from 208 to 218, inclusive. Also provided are various forms of vaccinia virus A41L proteins, including a protein comprising amino acids x to y of SEQ ID NO:3, 4, 5 or 6, wherein x represents an integer from 1 to 26, inclusive, and y represents an integer from 209 to 219, inclusive, of SEQ ID NOs:3, 4, 5, or 6, as well as various forms of variola virus A41L proteins, including a protein comprising amino acids x to y of SEQ ID NO:7, 8, or 9, wherein x represents an integer from 1 to 26, inclusive, and y represents an integer from 208 to 218, inclusive, of SEQ ID NOs:7, 8, or 9.

Although a protein encoded by an A41L ORF has not been purified from virally infected cells, when the A41L ORF is expressed recombinantly, it is a secreted protein. Accordingly, it is believed that non-recombinant A41L may be purified from the culture supernatant of cells infected with A41L-encoding viruses, as described below. Expression and purification of recombinant A41L is also discussed further below.

LAR-binding fragments of A41L polypeptides may be employed in the present invention. The ability of an A41L fragment (or any other A41L polypeptide) to bind LAR can be confirmed using a binding assay such as those described in examples 3 and 4. A41L fragments may be prepared by any of a number of conventional techniques. A desired DNA sequence may be chemically synthesized, for example. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction (PCR) procedure also may be employed to isolate a DNA sequence encoding a desired protein fragment. Oligonucleotides that define the termini of the desired fragment are employed as 5' and 3' primers in such a PCR procedure. As a further alternative, known mutagenesis techniques may be employed to insert a stop codon at a desired point, e.g., immediately downstream of the codon for the last amino acid of a desired fragment.

The present invention provides purified A41L polypeptides, both recombinant and non-recombinant. Variants and derivatives of native A41L proteins that retain the desired biological activity (e.g., the ability to bind LAR) are also within the scope of the present invention. A41L variants may be obtained by mutations of nucleotide sequences coding for native A41L polypeptides, for example. An A41L variant, as referred to herein, is a polypeptide substantially homologous to a native A41L, but which has an amino acid sequence different from that of a native A41L because of one or more deletions, insertions or substitutions, and exhibits the desired LAR-binding property. A41L polypeptides, variants and derivative provided herein include, but are not limited to, fragments, analogs and variants of the native A41L proteins of SEQ ID NOs:2 through 9. Such analogs are discussed in more detail below.

The variant amino acid sequence preferably is at least 80% identical, more preferably at least 90%, most preferably at least 95% identical to a native A41L amino acid sequence (such as the sequence of SEQ ID NO:2, 4, or 6. Variant nucleic acids provided herein are preferably at least 80% identical, more preferably at least 90%, most preferably at least 95% identical to a native A41L DNA sequence (such as the sequence of SEQ ID NO:1). In one embodiment of the present invention, A41L DNA and amino acid sequences are at least 80% identical (preferably at least 90% identical, more preferably at least 95%) to the DNA sequence of SEQ ID NO:1 or the amino acid sequence presented in SEQ ID NO:2. In other embodiments of the invention, the amino acid sequence of the A41L protein is at least 90%, at least 91%, at least 92%, at least 93%, at least 94%, at least 95%, at least 96%, at least 97%, at least 98%, or at least 99% identical to the amino acid sequence presented in SEQ ID NO:2.

Percent identity is defined as the number of aligned symbols, i.e. nucleotides or amino acids, which are identical, divided by the total number of symbols in the shorter of the two sequences. The degree of homology (percent identity) between two sequences may be determined by using the alignment method of Needleman and Wunsch (*J. Mol. Biol.* 48:443, 1970) as revised by Smith and Waterman (*Adv. Appl. Math* 2:482, 1981), with a unary comparison matrix (containing a value of 1 for identities and 0 for nonidentities) for nucleotides, and the weighted comparison matrix of Gribskov and Burgess (*Nucl. Acids Res.* 14:6745, 1986) as described by Schwartz and Dayhoff (*Atlas of Protein Sequence and Structure*, National Biomedical Research Foundation, pp. 353–358, 1979) for amino acids.

Preferably, the comparison is done using a computer program. An exemplary, preferred computer program is the Genetics Computer Group (GCG; Madison, Wis.) Wisconsin package version 10.0 program, 'GAP.' The preferred default parameters for the 'GAP' program includes: (1) The GCG implementation of the previously stated comparison matrixes for nucleotides and amino acids; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by one skilled in the art of sequence comparison may also be used.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Methods of making the alterations set forth above are disclosed by Walder et al. (*Gene* 42:133, 1986); Bauer et al. (*Gene* 37:73, 1985); Craik (*BioTechniques*, Jan. 12–19, 1985); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Conservatively substituted A41L polypeptides encompassed by the present invention are those that retain the ability to bind LAR. Certain embodiments of A41L proteins contain from one to ten conservative amino acid substitutions.

One embodiment of the present invention is directed to an A41Lpolypeptide comprising conservative substitution(s) in the amino acid sequence presented in SEQ ID NO:2, wherein the conservatively substituted polypeptide exhibits a biological activity that is essentially equivalent to that of the native protein of SEQ ID NO:2. Those of skill in the art will be guided in selecting amino acid residues for substitution by comparing the amino acid to be substituted with those shown for various A41L proteins in FIG. 1. Thus, for example, a Cys at amino acid residue 11 of a vaccinia or variola virus A41L protein could be substituted with another amino acid, for example a Gly as is found in CPV. Alternatively (or additionally), the Tyr at amino acid residue 114 of a variola virus A41L polypeptide could be substituted with another amino acid, for example, a His as is found in the corresponding location in CPV and vaccinia A41L polypeptides.

A41L also may be modified to create derivatives by forming covalent or aggregative conjugates with other chemical moieties, such as glycosyl groups, lipids, phosphate, acetyl groups and the like. Covalent derivatives of A41L may be prepared by linking the chemical moieties to functional groups on A41L amino acid side chains or at the N-terminus or C-terminus of an A41L polypeptide. Other derivatives of A41L within the scope of this invention include covalent or aggregative conjugates of A41L or its fragments with other proteins or polypeptides, such as by synthesis in recombinant culture as N-terminal or C-terminal fusions.

An A41L protein may be treated or derivatized to reduce the immunogenicity and antigenicity thereof. Such modification may be desirable if A41L is to be administered repeatedly to an individual, e.g., to treat a chronic condition. One approach involves attaching the polymer polyethylene glycol (PEG) to an A41L protein. Chemical modification with PEG has reduced the immunogenicity or antigenicity of a number of proteins (See Katre, N., *J. Immunol.* 144:209, 1990; and Delgado et al., *Critical Reviews in Therapeutic Drug Carrier Systems,* 9:249, 1992.) Modification with PEG has also been reported to increase the serum half-life and solubility of certain proteins. PEG may be covalently linked to lysine residues, to carbohydrate moieties on glycosylated proteins, or selectively to the N-terminus of proteins, for example. Modified A41L proteins can be tested in a suitable binding assay to confirm that the desired LAR-binding property is retained.

Fragments of A41L may be less immunogenic than the corresponding full length proteins. The glycosylation pattern may affect the immunogenicity of a protein. As discussed above, glycosylation of recombinant proteins may be altered through the choice of host cells.

A41L polypeptide fusions can comprise peptides added to facilitate purification and identification of A41L(referred to as 'tag' peptides). Such peptides include, for example, poly-His or the antigenic identification peptides described in U.S. Pat. No. 5,011,912 and in Hopp et al., *Bio/Technology* 6:1204, 1988. Additional, useful tag proteins include green fluorescent protein (GFP; Chalfie et al., *Science* 263:802, 1994), an N-terminal peptide that contains recognition sites for a monoclonal antibody, a specific endopeptidase, and a site-specific protein kinase (PKA; Blanar and Rutter, *Science* 256:1014, 1992), birA (Altman et al., *Science* 274:94, 1996).and glutathione S transferase (GST: Smith and Johnson, *Gene* 67:31, 1988).

A very useful tag peptide is the FLAG® peptide (SEQ ID NO:11), disclosed in U.S. Pat. No. 5,011,912 and in Hopp et al., which is highly antigenic and provides an epitope reversibly bound by a specific monoclonal antibody enabling rapid assay and facile purification of expressed recombinant protein. This sequence is also specifically cleaved by bovine mucosal enterokinase at the residue immediately following an Asp-Lys pairing. Fusion proteins capped with this peptide may also be resistant to intracellular degradation in *E. coli.* A murine hybridoma designated 4E11 produces a monoclonal antibody that binds the FLAG® peptide in the presence of certain divalent metal cations (as described in U.S. Pat. No. 5,011,912) and has been deposited with the American Type Culture Collection under accession no BB 9259.

The present invention further includes A41L polypeptides with or without associated native-pattern glycosylation. A41L expressed in yeast or mammalian expression systems (e.g., COS-7 cells) may be similar to or significantly different from a native A41L polypeptide in molecular weight and glycosylation pattern, depending upon the choice of expression system. Expression of A41L polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, N-glycosylation sites in A41L can be modified to preclude glycosylation, allowing expression of a more homogeneous, reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. CPV A41L comprises a potential glycosylation site at amino acid residue 71 (which corresponds to amino acid residue 70 in vaccinia or variola virus). Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, codons for Cys residues that are not essential for biological activity can be altered to cause the Cys residues to be deleted or replaced with other amino acids. Formation of incorrect intramolecular disulfide bridges upon renaturation is thus prevented. The A41L protein of SEQ ID NOs:3 through 9 comprises nine Cys residues, and the A41L protein of SEQ ID NO:2 comprises 8 Cys residues. Accordingly, the first Cys residue (at amino acid 11 of SEQ ID 3 through 9) may be deleted or substituted with another amino acid.

The present invention provides both non-naturally occurring and naturally occurring biologically active A41L variants. Examples of naturally occurring variants are proteins that result from proteolytic cleavage of the A41L protein, wherein the ability to bind LAR is retained. Variations attributable to proteolysis include, for example, differences in the N- or C-termini upon expression in different types of host cells, due to proteolytic removal of one or more terminal amino acids from the A41L protein (generally from 1–5 terminal amino acids). Naturally occurring variations in the DNA sequence may include silent mutations, for example, or deletions that do not result in a shift in the reading frame.

Due to the known degeneracy of the genetic code wherein more than one codon can encode the same amino acid, a DNA sequence may vary from that presented in SEQ ID NO:1, and still encode an A41L protein having the amino acid sequence of SEQ ID NO:2. Such variant nucleic acids may result from silent mutations (e.g., occurring during PCR amplification), and may be the product of deliberate mutagenesis of a native sequence.

Particular embodiments of A41L-encoding DNAs are isolated DNAs comprising nucleotides 1 to 654 or 58 to 654 of SEQ ID NO:1. The DNA that comprises nucleotides 1 to 654 of SEQ ID NO:1 encodes a cowpox A41L protein that includes the native signal peptide, whereas a DNA having the sequence of nucleotides 58 to 654 encodes the predicted, mature form of the protein. The invention further provides various forms of cowpox A41L DNAs, including a DNA comprising nucleotides x to y of SEQ ID NO:1, wherein x represents an integer from 1 to 73 (preferably, from 1 to 58), inclusive, and y represents an integer from 621 to 654, inclusive.

Disclosed herein are isolated nucleic acids encoding biologically active A41L, selected from: (a) the nucleotide sequence presented in SEQ ID NOS:1 or 3; (b) DNA capable of hybridization to a nucleotide sequence of (a) under moderately or severely stringent conditions and which encodes a biologically active A41L; and (c) DNA which is degenerate as a result of the genetic code to the nucleotide sequence defined in (a) or (b). The A41L proteins encoded by such nucleic acids are encompassed by the present invention.

Nucleic acid sequences disclosed herein include isolated DNA and RNA sequences that hybridize to native A41L nucleotide sequences under conditions of moderate or severe stringency, and which encode biologically active A41L. For use in the therapeutic methods of the present invention, the desired biological activity of the encoded A41L is the ability to bind LAR. Moderately stringent hybridization conditions refer to conditions described in, for example, Sambrook et al. *Molecular Cloning: A Laboratory Manual,* 2 ed. Vol. 1, pp. 1.101–104, Cold Spring Harbor Laboratory Press, (1989). Conditions of moderate stringency, as defined by Sambrook et al., include use of a prewashing solution of 5×SSC, 0.5% SDS, 1.0 mM EDTA (pH 8.0) and hybridization at about 55 degrees C., 5×SSC, overnight, followed by washing at 50–55 degrees C. in 2 ×SSC, 0.1% SDS. Conditions of severe stringency include higher temperatures of hybridization and washing, in lower salt. The skilled artisan will recognize that the temperature and wash solution salt concentration may be adjusted as necessary according to factors such as the length of the probe. Examples of A41L-encoding nucleic acids include those that will hybridize to the nucleotide sequence of SEQ ID NOS:1, 3, or 5, under severely stringent conditions that include hybridization at 68 degrees C. followed by washing in 0.1×SSC/0.1% SDS at 63–68 degrees C.

Examples of A41L proteins encoded by DNA that varies from the native DNA sequence of SEQ ID NOS:1, 3, or 5, wherein the variant DNA will hybridize to the native DNA sequence under moderately or severely stringent conditions, include, but are not limited to, A41L fragments and A41L proteins comprising inactivated N-glycosylation site(s), or conservative amino acid substitution(s), as described above. A41L proteins encoded by DNA derived from organisms other than cowpox virus, wherein the DNA will hybridize to the DNA of SEQ ID NO:1, are also encompassed.

Variants possessing the requisite ability to bind LAR may be identified by any suitable assay. A biosensor unit may be employed, as described in example 2. Alternatively, biological activity of an A41L variant may be determined by competition with a native A41L (e.g., the A41L of SEQ ID NO:2) for binding to a given LAR (i.e. competitive binding assays). One type of a competitive binding assay employs an A41L/Fc fusion protein bound to a solid phase through the interaction of the Fc moiety with Protein A or Protein G affixed to the solid phase. The ability of an A41L variant to inhibit binding of a labeled LAR to the immobilized A41L/Fc is analyzed by conventional techniques. Variants capable of binding LAR find use, e.g., for LAR or treating a disease mediated by LAR.

A41L polypeptides may be employed as reagents in vitro assays. One example involves the use of A41L in screening assays to detect or isolate LAR in a biological sample or cell culture. Similarly, LAR polypeptides, particularly soluble forms of LAR, may be used as reagents in vitro assays.

Soluble forms of LAR include a peptide comprising amino acids x to y, wherein x represents an integer from 1 to 20, inclusive, and y represents an integer from 960 to 965, inclusive, of SEQ ID NO:10; additional soluble forms of LAR comprise amino acids x to y, wherein x represents an integer from 1 to 20, inclusive, and y represents an integer from 302 to 312, inclusive, of SEQ ID NO:10, or amino acids x to y, wherein x represents an integer from 1 to 24, inclusive, and y represents an integer from 302 to 322, inclusive, of SEQ ID NO:10. Additional soluble forms of LAR include polypeptides comprising amino acids x to y, wherein x represents an integer from 1 to 24, inclusive, and y represents an integer from 296 to 306, inclusive, of SEQ ID NO:12; and polypeptides comprising amino acids x to y, wherein x represents an integer from 1 to 20, inclusive, and y represents an integer from 296 to 306, inclusive, of SEQ ID NO:12. Fragments of the aforementioned polypeptides comprising the immunoglobulin domains of LAR (amino acids 44 through 294 of SEQ ID NO:10; amino acids 44 through 288 of SEQ ID NO:12) can also be prepared and evaluated for the ability to bind an A41L polypeptide.

Fragments of such polypeptides will also be useful in assays, and as antagonists of LAR in vivo or in vitro. Moreover, variants of LAR are also comprehended herein. Such variants include those described above for A41L polypeptides (i.e., non-naturally occurring and naturally occurring biologically active LAR variants, LAR polypeptides encoded by isolated DNA and RNA sequences that hybridize to native LAR nucleotide sequences under conditions of moderate or severe stringency, and LAR polypeptides comprising various additions or substitutions of amino acid residues or sequences, or deletions of terminal or internal residues or sequences not needed for biological activity, for example, alteration of glycosylation sites or Cys residues not needed for biological activity).

The variant amino acid sequence preferably is at least 80% identical, more preferably at least 90%, most preferably at least 95% identical to a native LAR amino acid sequence (such as the sequence of SEQ ID NO:10 or 12. Variant nucleic acids provided herein are preferably at least 80% identical, more preferably at least 90%, most preferably at least 95% identical to a native LAR DNA sequence (such as the sequence of SEQ ID NO:10 or 12). In one embodiment of the present invention, LAR DNA and amino acid sequences are at least 80% identical (preferably at least 90% identical, more preferably at least 95%) to the DNA sequence of SEQ ID NO:10 or the amino acid sequence presented in SEQ ID NO:12. In other embodiments of the invention, the amino acid sequence of the LAR polypeptide is at least 90%, at least 91%, at least 92%, at least 93%, at least 94%, at least 95%, at least 96%, at least 97%, at least 98%, or at least 99% identical to the amino acid sequence presented in SEQ ID NOs:10 or 12. Nucleic acids encoding the aforementioned polypeptides are also included within the scope of the invention.

Expression Systems

The present invention provides recombinant expression vectors for expression of A41L and/or LAR polypeptides, and host cells transformed with the expression vectors. Any suitable expression system may be employed. The vectors include an A41L DNA or a LAR DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the A41L or LAR DNA sequence. Thus, a promoter nucleotide sequence is operably linked to an A41L or LAR DNA sequence if the promoter nucleotide sequence controls the transcription of the A41L or LAR DNA sequence. The ability to replicate in the desired host cells, usually conferred by an origin of replication, and a selection gene by which transformants are identified, may additionally be incorporated into the expression vector.

If desired, a native signal sequence may be replaced with a heterologous signal sequence. A signal peptide that promotes higher levels of secretion from a particular type of host cells than does the native signal peptide may be chosen, for example. A DNA sequence encoding the heterologous signal peptide (secretory leader) is fused in frame to the A41L or LAR sequence so that the encoded polypeptide is initially translated as a fusion protein comprising the signal peptide. The signal peptide is cleaved from the polypeptide upon secretion of the polypeptide from the cell.

Suitable host cells for expression of A41L and/or LAR polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce such polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, an A41L or a LAR polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and an A41L DNA (or LAR DNA) sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda$ $P_L$ promoter and a cI857ts thermolabile repressor sequence. Plasmid vectors available from the American Type Culture Collection which incorporate derivatives of the $\lambda$ $P_L$ promoter include plasmid pHUB2 (resident in *E. coli* strain JMB9 (ATCC 37092)) and pPLc28 (resident in *E. coli* RR1 (ATCC 53082)).

Recombinant polypeptides alternatively may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2$\mu$ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the polypeptide. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those skilled in the pertinent field.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Depression of the ADH2 promoter occurs when glucose is exhausted from the medium.

Mammalian or insect host cell culture systems could also be employed to express recombinant polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells is described by Cosman et al. (*Mol. Immunol.* 23:935, 1986). A high expression vector, PMLSV N1/N4, described by Cosman et al., *Nature* 312:768, 1984 has been deposited as ATCC 39890. Additional suitable mammalian expression vectors are described in EP-A-0367566, and in PCT application WO 91/18982. In one embodiment, the vectors are derived from retroviruses.

A native A41L signal peptide is employed in the expression system described in example 1. Alternatively, DNA encoding a heterologous signal sequence (e.g., derived from a mammalian protein) may be added. Examples include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460, 846.

A41L and LAR Proteins and Uses Thereof

The present invention provides purified A41L polypeptides, which may be produced by recombinant expression systems as described above or purified from naturally occurring, virally infected cells. Recombinant expression systems may be preferred for purification of certain A41L proteins due to the infective nature of the virus from which they are derived. The invention further provides purified LAR polypeptides, which may be produced by recombinant expression systems as described above. The desired degree of purity depends on the intended use of the protein. A relatively high degree of purity is desired when the protein is to be administered in vivo, for example.

Advantageously, the polypeptides of the invention are purified such that no protein bands corresponding to other proteins are detectable by SDS-polyacrylamide gel electrophoresis (SDS-PAGE). It will be recognized by one skilled in the pertinent field that multiple bands corresponding to A41L protein (or LAR protein) may be detected by SDS-PAGE, due to differential glycosylation, variations in post-translational processing, and the like. A preparation of A41L protein is considered to be purified as long as no bands corresponding to different (non-A41L) proteins are visualized; similarly, for preparations of LAR proteins, as no bands corresponding to different (non-LAR) proteins are visualized. The proteins of the invention are most preferably purified to substantial homogeneity, as indicated by a single protein band upon analysis by SDS-PAGE. The protein band may be visualized by silver staining, Coomassie blue staining, or (if the protein is radiolabeled) by autoradiography.

One process for producing the polypeptides of the invention comprises culturing a host cell transformed with an expression vector comprising a DNA sequence that encodes said polypeptides under conditions such that a desired polypeptide (A41L or LAR) is expressed. The protein is then recovered from the cell culture, using standard procedures. Advantageously, the expression vector encodes a signal peptide fused to the N-terminus of the protein, such that the protein is secreted from the host cell and may be recovered from the culture medium.

For example, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify A41L. Some or all of the foregoing purification steps, in various combinations, can be employed to provide a substantially homogeneous recombinant protein.

It is also possible to utilize an immunoaffinity column containing an antibody that binds A41L to purify this polypeptide. Example 5 describes a procedure for employing an A41L protein to generate monoclonal antibodies reactive therewith. Similar procedures could be used to generate monoclonal antibodies that bind LAR, which could then be used in affinity purification thereof. Moreover, A41L can be used to affinity-purify LAR, and LAR can be used to affinity purify A41L, based on their interaction.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed host cells are preferably employed to express A41L (or LAR) as a secreted polypeptide. This simplifies purification. Secreted recombinant polypeptide from a host cell can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

In one embodiment of the invention, non-recombinant A41L is purified by procedures analogous to those described herein for recombinant A41L proteins. Briefly, suitable cells (e.g., rabbit kidney cells or CV1 cells) are infected with cowpox virus, vaccinia virus (for example, strain Copenhagen, or another strain) or variola virus (for example, strain India-1966 or another strain), and incubated to allow secretion of A41L from the cells. The culture supernatant is collected, cells are removed (e.g., by centrifugation), and the supernatant is applied to a suitable purification resin (for example, an antibody affinity column). Proteins are eluted from the column by suitable methods, and the fraction containing the desired A41L protein is recovered.

Certain uses of A41L polypeptides flow from the ability to bind LAR. One such use of A41L is as a reagent in protein purification procedures. A41L or A41LUFc fusion proteins may be attached to a solid support material by conventional techniques and used to purify LAR by affinity chromatography. This use is illustrated in example 2.

A41L also finds use in modulating the biological activity of LAR. This use stems from the unexpected finding that A41L binds to LAR, as reported in example 3.

The present invention provides a method of treating a disorder mediated by LAR, comprising administering an effective amount of an A41L polypeptide to a mammal afflicted with such a condition. Any of the forms of A41L polypeptides described herein may be employed, including, but not limited to, native A41L proteins and variants, derivatives, oligomers, and biologically active fragments thereof, as well as fusion proteins comprising A41L. In particular embodiments of the invention, the mature form of the cowpox A41L of SEQ ID NO:2, the vaccinia virus A41L of SEQ ID NOs:4 through 7, or the variola (smallpox) A41L of SEQ ID NOs:8 through 10 is employed.

A disorder is said to be mediated by LAR if LAR causes or promotes, at least in part, or exacerbates the disorder. LAR may cause a condition indirectly, for example by modulating one or more pathways that regulate cytokine receptor signaling. Alternatively, LAR may cause or promote a condition in a more direct manner, for example via its interaction with the insulin receptor.

Because A41L is a virulence factor (that is, it is required for proliferation of a poxvirus in a host animal but not for proliferation of a poxvirus in vitro), it plays a role in regulating the immune and/or inflammatory response. . A role for LAR in modulating a host immune or inflammatory response is supported by the finding that it dephosphorylates JAK2, similar to CD45 (Irie-Sasaki et al., supra). Accordingly, A41L will have use in modulating an immune and/or inflammatory response. Moreover, the interaction of A41L and LAR serves as mechanism by which to identify additional regulators of an immune and/or inflammatory response, as described herein. Compounds that inhibit the interaction of A41L and LAR (identified as described herein) will also be useful in treating or ameliorating poxvirus infections by preventing the virulence factor (A41L) from binding its counterstructure in the infected host.

Moreover, the expression and/or activity of PTPs, including LAR, is known to be increased in obesity and Type 2 diabetes (see, for example, Zabolotny et al., *Proc. Natl. Acad. Sci. USA* 98:5187, 2001). Accordingly, the interaction of A41L and LAR will be useful in identifying compounds that can be used to regulate insulin signaling, which will be useful in treatment of conditions in which the over-expression or hyperactivity of PTPs plays a role (i.e., obesity and/or insulin resistance).

Additionally, a potential role for LAR in the proliferation of cells may also indicate a use for a method that employs the interaction of LAR and A41L to identify compounds that regulate cell proliferation. For example, the association of the region of the human chromosome to which LAR has been mapped with tumors of neuroectodermal origin and the association of changes in expression of LAR with the ability of cells to proliferate suggest that a compound that modulates the activity of LAR may be useful in regulating cell growth (either in tumor cells or neural cells). Moreover, differential splicing of LAR appears to be developmentally regulated. Accordingly, reagents specific for certain forms of LAR will be useful in diagnostic or therapeutic applications relevant to the particular form for which they are specific.

The A41L (or other, identified compound) preferably is administered in the form of a pharmaceutical composition. Such compositions can be formulated according to known methods that are used to prepare pharmaceutically useful compositions. Components that are commonly employed in pharmaceutical formulations are described in Remington's Pharmaceutical Sciences, 16th ed., 1980, Mack Publishing Company, for example.

Compositions of the present invention comprise an effective amount of a purified compound (i.e., a purified A41L polypeptide, a purified LAR polypeptide, or a compound that modulates the interaction of A41L and LAR) and a suitable (e.g., pharmaceutically acceptable) diluent, excipient, or carrier. Such carriers will be essentially non-toxic (minimally toxic) to patients at the dosages and concentrations employed. The composition may additionally include a suitable emulsifier or preservative. Ordinarily, the preparation of such compositions may entail combining an A41L polypeptide with buffers, antioxidants such as ascorbic acid, low molecular weight (less than about 10 residues) peptides, proteins, amino acids, carbohydrates including glucose, sucrose, or dextrans, chelating agents such as EDTA, glutathione, or other stabilizers and excipients. Neutral buffered saline is one appropriate diluent. Pharmaceutical compositions suitable for inhalation are among the compositions contemplated herein.

Useful compounds may be incorporated into polymeric compounds (such as polyacetic acid, polyglycolic acid, hydrogels, dextran, etc.) or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of A41L, and are thus chosen according to the intended application.

For therapeutic use, the compositions are administered in a manner and dosage appropriate to the indication and the patient. The amount administered will be effective in ameliorating the condition, by modulating (inhibiting or increasing, as needed for the indication) the activity of LAR in vivo. As will be understood by one skilled in the pertinent field, a therapeutically effective dosage will vary according to such factors as the nature and severity of the condition, the location of affected tissue (e.g., the site of inflammation) within the body, and the age, condition and size of the patient. Administration may be by any suitable route, depending on the nature of the disorder, including but not limited to intravenous or local injection, inhalation, continuous infusion, local infusion during surgery, or sustained release from implants (such as gels, membranes, and the like).

Oligomeric Forms of A41L and/or LAR Polypeptides

The present invention encompasses polypeptides (either A41L or LAR) in the form of oligomers, such as dimers, trimers, or higher oligomers. Oligomers may be formed by disulfide bonds between cysteine residues on different polypeptides, for example. In other embodiments, oligomers comprise from two to four polypeptides joined by covalent or non-covalent interactions between peptide moieties fused to the polypeptides. Such peptide moieties may be peptide linkers (spacers), or peptides that have the property of promoting oligomerization. Leucine zippers and certain polypeptides derived from antibodies are among the peptides that can promote oligomerization of polypeptides attached thereto. Nucleic acids encoding oligomers, or fusion proteins that are components of such oligomers, are provided herein.

Preparation of fusion proteins comprising heterologous polypeptides fused to various portions of antibody-derived polypeptides (including the Fc domain) has been described, e.g., by Ashkenazi et al. (*PNAS USA* 88:10535, 1991), Byrn et al. (*Nature* 344:667, 1990), and Hollenbaugh and Aruffo ("Construction of Immunoglobulin Fusion Proteins", in *Current Protocols in Immunology, Suppl.* 4, pages 10.19.1–10.19–11, 1992), hereby incorporated by reference. In one embodiment of the invention, an A41L (or LAR) dimer is created by fusing A41L (or LAR, respectively) to an Fc region polypeptide derived from an antibody (yielding a fusion protein), in a manner that does not interfere with binding of A41L to LAR. A gene fusion encoding the fusion protein is inserted into an appropriate expression vector. The fusion proteins are allowed to assemble much like antibody molecules, whereupon interchain disulfide bonds form between Fc polypeptides, yielding divalent A41L.

One suitable Fc polypeptide is the native Fc region polypeptide derived from a human IgG1, which is described in PCT application WO 93/10151, hereby incorporated by reference. Another useful Fc polypeptide is the Fc mutein described in U.S. Pat. No. 5,457,035. The amino acid sequence of the mutein is identical to that of the native Fe sequence presented in WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

In other embodiments, A41L (or LAR) may be substituted for the variable portion of an antibody heavy or light chain. If fusion proteins are made with both heavy and light chains of an antibody, it is possible to form an oligomer with as many as four A41L (or LAR) polypeptides.

Alternatively, oligomeric A41L (or LAR) may comprise two or more A41L (or LAR) polypeptides joined through peptide linkers. Examples include those peptide linkers described in U.S. Pat. No. 5,073,627 (hereby incorporated by reference). Fusion proteins comprising multiple polypeptides separated by peptide linkers may be produced using conventional recombinant DNA technology.

Another method for preparing oligomers involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize. Examples of leucine zipper domains suitable for producing A41L oligomers are those described PCT application WO 94/10308, hereby incorporated by reference. Recombinant fusion proteins comprising a polypeptide (for example, A41L or LAR) fused to a peptide that dimerizes or trimerizes in solution are expressed in suitable host cells, and the resulting soluble oligomeric A41L is recovered from the culture supernatant.

Antibodies

Antibodies that are immunoreactive with the polypeptides disclosed herein are also provided, including antibodies that bind A41L polypeptide, and antibodies that bind LAR polypeptides. Such antibodies specifically bind to the respective polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology. An exemplary epitope is the six-amino acid insert represented by amino acid 181 through 186 of SEQ ID NO:10, which does not appear to be present in other, alternatively-spliced forms of LAR. Antibodies that recognize this epitope would thus be specific for the form of LAR depicted in SEQ ID NO:10, and would not bind other forms.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide or a DNA encoding a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*Proc. Natl. Acad. Sci. USA* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')2 fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

In one embodiment of the invention, antibodies to LAR are antagonistic, that is, they bind LAR and prevent the binding of a counterstructure to LAR, thereby inhibiting the activity of LAR. Such antagonistic antibodies to LAR would be useful in upregulating an immune or inflammatory response (for example, in an individual suffering from or at risk for infection by a pathogenic or opportunistic organism, as a vaccine adjuvant, and/or in treatment of cancer). Antagonists of LAR are also useful decreasing other undesirable activities of LAR, for example, in conditions where insulin resistance plays a role (for example, obesity, Type 2 diabetes, etc.).

In another embodiment of the invention, antibodies to LAR are agonistic, that is, they bind LAR and stimulate the activity of LAR. Such agonistic antibodies to LAR would be useful in downregulating an immune or inflammatory response (for example, in autoimmune or inflammatory disease, including atherosclerosis, arthritis, multiple sclerosis (MS), systemic lupus erythematosous (SLE), thrombosis, graft versus host disease, graft rejection and sepsis). Agonists of LAR will also find utility in increasing the activity of LAR in conditions wherein LAR activity is decreased (for example, in some tumors, or at certain points during neural development).

Nucleic Acid Fragments

The present invention further provides fragments of the A41L nucleotide sequences presented herein. Such fragments desirably comprise at least about 17 consecutive nucleotides, more preferably at least 30 consecutive nucleotides of the sequence presented in SEQ ID NO:1, or DNAs encoding the peptides of SEQ ID NOs:3 through 9. DNA and RNA complements of said fragments are provided herein, along with both single-stranded and double-stranded forms of A41L DNA.

Among the uses of such A41L nucleic acid fragments is use as a probe. Such probes may be employed in cross-species hybridization procedures to isolate A41L DNA from additional viral strains. The probes also find use in detecting the presence of A41L nucleic acids in in vitro assays and in such procedures as Northern and Southern blots. Cell types expressing A41L can be identified. Such procedures are well known, and the skilled artisan can choose a probe of suitable length, depending on the particular intended application. The probe may be labeled (e.g., with $^{32}P$) by conventional techniques.

A41L nucleic acid fragments also find use as primers in a polymerase chain reaction (PCR). 5' and 3' primers corresponding to the termini of a desired A41L DNA sequence are employed in isolating and amplifying the DNA, using conventional PCR techniques.

Similarly, LAR nucleic acid fragments will also find use as probes or primers, and will preferably comprise at least about 17 consecutive nucleotides, more preferably at least 30 consecutive nucleotides of the sequence encoding LAR. For example, a probe comprising the nucleic acid of SEQ ID NO:13 can be used to detect the presence of nucleic acids encoding the unique splice variant of SEQ ID NO:10 in specimens, while a primer comprising SEQ ID NO:13 can be used to isolate and/or amplify such DNAs, as described previously.

Screening Assays Utilizing A41L and LAR

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochermiluminescence, as well as more traditional heterogeneous assay formats such as enzyme-linked immunosorbant assays (ELISA) or radioimmunoassays. Also comprehended herein are cell-based assays, for example those utilizing reporter genes, as well as functional assays that analyze the effect of an antagonist or agonist on biological function(s).

Moreover, combinations of screening assays can be used to find molecules that regulate the biological activity of A41L and/or LAR. Molecules that regulate the biological activity of a polypeptide may be useful as agonists or antagonists of the peptide. In using combinations of various assays, it is usually first determined whether a candidate molecule binds to a polypeptide by using an assay that is amenable to high throughput screening. Binding candidate molecules identified in this manner are then added to a biological assay to determine biological effects. Molecules that bind and that have an agonistic or antagonistic effect on biologic activity will be useful in treating or preventing disease or conditions with which the polypeptide(s) are implicated.

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions (including protein-protein, receptor-ligand, enzyme-substrate, and so on), and the inhibition thereof by small organic molecules. These assay methods and techniques are well known in the art (see, e.g., High Throughput Screening: The Discovery of Bioactive Substances, John P. Devlin (ed.), Marcel Dekker, New York, 1997 ISBN: 0-8247-0067-8). The screening assays of the present invention are amenable to high throughput screening of chemical libraries and are suitable for the identification of small molecule drug candidates, antibodies, peptides, and other antagonists and/or agonists, natural or synthetic.

One such assay is based on fluorescence resonance energy transfer (FRET; for example, HTRF®, Packard Instrument Company, Meriden, CT; LANCE™, PerkinElmer LifeSciences, Wallac Oy., Turku, Finland) between two fluorescent labels, an energy donating long-lived chelate label and a short-lived organic acceptor. The energy transfer occurs when the two labels are brought in close proximity via the molecular interaction between A41L and LAR. In a FRET assay for detecting inhibition of the binding of A41L and LAR, europium chelate or cryptate labeled A41L or LAR serves as an energy donor and streptavidin-labeled allophycocyanin (APC) bound to the appropriate binding partner (i.e., A41L if LAR is labeled, or LAR if A41L is labeled) serves as an energy acceptor. Once A41L binds LAR, the donor and acceptor molecules are brought in close proximity, and energy transfer occurs, generating a fluorescent signal at 665 nm. Antagonists of the interaction of A41L and LAR will thus inhibit the fluorescent signal, whereas agonists of this interaction would enhance it.

Another useful assay is a bioluminescence resonance energy transfer, or BRET, assay, substantially as described in Xu et al., *Proc. Natl. Acad. Sci. USA* 96:151 (1999). Similar to a FRET assay, BRET is based on energy transfer from a bioluminescent donor to a fluorescent acceptor protein. However, a green fluorescent protein (GFP) is used as the acceptor molecule, eliminating the need for an excitation light source. Exemplary BRET assays include BRET and $BRET^2$ from Packard BioScience, Meriden, Conn.

DELFIA® (dissociated enhanced lanthanide fluoroimmunoassay; PerkinElmer LifeSciences, Wallac Oy., Turku, Finland) is a solid-phase assay based on time-resolved fluorometry analysis of lanthanide chelates (see, for example, U.S. Pat. No. 4,565,790, issued Jan. 21, 1986). For this type of assay, microwell plates are coated with a first protein (A41L or LAR). The binding partner (LAR or A41L, respectively) is conjugated to europium chelate or cryptate, and added to the plates. After suitable incubation, the plates are washed and a solution that dissociates europium ions from solid phase bound protein, into solution, to form highly fluorescent chelates with ligands present in the solution, after which the plates are read using a reader such as a $VICTOR^2$™ (PerkinElmer LifeSciences, Wallac Oy., Turku, Finland) plate reader to detect emission at 615 nm).

Another assay that will be useful in the inventive methods is a FlashPlate® (Packard Instrument Company, IL)-based assay. This assay measures the ability of compounds to inhibit protein-protein interactions. FlashPlates® are coated with a first protein (either A41L or LAR), then washed to remove excess protein. For the assay, compounds to be tested are incubated with the second protein (A41L, if the plates are coated with LAR, or LAR if plates are coated with A41L) and $I^{125}$ labeled antibody against the second protein and added to the plates. After suitable incubation and washing, the amount of radioactivity bound is measured using a scintillation counter (such as a MicroBeta® counter; PerkinElmer LifeSciences, Wallac Oy., Turku, Finland).

The AlphaScreen™ assay (Packard Instrument Company, Meriden, Conn.). AlphaScreen™ technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proxirmity to the donor bead (i.e., by virtue of the interaction of A41L and LAR), the singlet-state oxygen molecules reacts with chemiluminescent groups in the acceptor beads, which immediately transfer energy to fluorescent acceptors in the same bead. These fluorescent acceptors shift the emission wavelength to 520–620 nm, resulting in a detectable signal. Antagonists of the interaction of A41L and LAR will thus inhibit the shift in emission wavelength, whereas agonists of this interaction would enhance it.

One embodiment of a method for identifying molecules which inhibit or antagonize an activity mediated by LAR involves adding a candidate molecule to a medium which contains cells that express A41L and LAR; changing the conditions of said medium so that, but for the presence of the candidate molecule, A41L would be bound to LAR, and observing the binding and stimulation or inhibition of a functional response. The activity of the cells that were contacted with the candidate molecule may then be compared with the identical cells that were not contacted and antagonists and agonists of the polypeptides of the instant invention may be identified. The measurement of biological activity may be performed by a number of well-known methods such as measuring the amount of protein present (e.g. an ELISA) or of the protein's activity. A decrease in biological stimulation or activation would indicate an antagonist. An increase would indicate an agonist.

Overall A41L Polypeptide Structure

U.S. patent application Ser. No. 09/697,872, filed Oct. 26, 2000 (incorporated by reference herein), discloses the cowpox virus (cpv) p35 polypeptide structure, which has the shape of a compact globular protein of approximately 55 Å×35 Å×30 Å. The molecule is composed primarily of two β sheets that are parallel to each other, two short ochelices and large loops connecting these secondary structure elements. Eight cysteines are involved in four disulfide bridges (Cys8-Cys185, Cys38-Cys223, Cys79-Cys124, Cys132-Cys171). The unfolding temperature of the cpv p35 molecule is 86° C. and the four disulfide bridges probably contribute to this high thermal stability. With the exception of Cys8, all the cysteines are located at the N- or C-terminus of beta strands. A serine rich sequence is part of a random coil structure at the N-terminus of the p35 molecule. The crystal structure of p35 (also referred to as viral CC-chemokine inhibitor or vCCI) was determined as described by Carfi et al., *Proc. Natl. Acad. Sci. USA* 96:12379 (1999).

The beta sandwich in which p35 polypeptides are folded is a structure of new topology, reminiscent of the collagen-binding domain from *Staphylococcus aureus* adhesin. Based on the presence of eight conserved cysteines in A41L, and the alignment of these residues with the eight conserved cysteines found in p35, A41L will have topology and structure similar to that of p35. Accordingly, the sequence of A41L was submitted to GeneFold (Tripos, Inc., St. Louis, Mo.; Berman et al., *Nucleic Acids Res* 28:235, 2000), a protein threading program that overlays a query protein sequence onto structural representatives of the Protein Data Bank (PDB) (Jaroszewski et al., *Prot Sci* 7:1431, 1998). This produced a very strong hit (999.9 in all three score types) to p35, indicating that A41L and P35 were structurally compatible and a structural model of A41L could be produced based on the structure of p35.

The Modeler software package from Molecular Simulations Inc. was used to create a family of ten structures. The structure model with the lowest probability density function (PDF) was chosen to represent the structure family; these results indicated that A41L and p35 do share significant structural and topological similarity.

When the amino acid sequences from nine different poxvirus A41L peptides are aligned, as shown in FIG. 1, it can be seen that very few deletions and insertions are required to align the A41L polypeptide sequences from the various sources. The poxvirus A41L polypeptides have at least about 90% sequence identity to CPV A41L, and all have the same number and pattern of conserved cysteines in the mature protein.

In view of the close alignment of the various A41L polypeptide shown in FIG. 1, the superimposable models, and the structural similarity of A41L with p35, the molecular coordinates provided in U.S. Ser. No. 09/697,872, defining the detailed molecular architecture of the cowpoxvirus (cpv) p35 polypeptide, are directly applicable to the molecular architecture of A41L and the analogous gene product of other poxviruses, including but not limited to, Variola virus (including strains India-1967, Garcia-1966, and Harvey), vaccinia virus (including Copenhagen, Tian Tan, Ankara and WR strains), as well as rabbitpox virus, Camelpox virus, Ectromelia (mousepoxvirus), and Fowlpox virus. Moreover, the molecular architecture of the analogous gene products in any other members of the poxvirus family will also be similar.

Moreover, knowledge of the molecular structure of the class of proteins represented by p35 and A41L will allow identification of which residues are important in binding different binding partners (or cognates). Just as definition of framework regions versus complementarity-determining regions in antibody molecules has facilitated the design and production of recombinant antibodies having desired characteristics (i.e., humanized antibodies that bind with high affinity to selected antigens), understanding of the molecular structure of the proteins described herein will facilitate design of molecules that mimic or inhibit the interactions of A41L and/or p35 (or related) proteins with proteins expressed by host cells.

Such design can be accomplished either by utilizing the molecules themselves in screening large numbers of compounds, or in computational approaches (also known as de novo drug or rational drug design). The crystal structure coordinates of a polypeptide are input for a computer program, such as DOCK. Programs such as DOCK output a list of small molecule structures that are expected to associate with a binding partner as determined by their ability to compete with viral polypeptides for binding with binding partners and their native cognates. Ultimately, molecules identified by the DOCK program can be synthesized and screened using appropriate binding assays.

Useful molecules may bind only A41L; such molecules are expected to have utility in modulating the binding of A41L and LAR. Molecules that bind both A41L and p35 can also be identified; they may be particularly useful as anti-viral agents (i.e., by binding to both pox virus virulence factors, A41L and p35).

Computer Analysis of Structure and/or Assay Results

In one aspect of the invention, the assays of the invention are used to identify compounds that alter an activity of LAR. In another aspect of the invention, the assays of the invention are used to identify compounds that alter an activity of A41L. The benefits of integrated robotic systems used to analyze collections of chemical compounds/natural products in such assays, which preferably incorporate high-throughput screening methods, are most often realized by the use of sophisticated computer and statistical techniques to manage the resulting data. In one form, the information generated in the inventive screening assays is stored (or compiled) in electronic form, using a computerized database that allows information to be efficiently catalogued and retrieved. Such databases are comprised of records, usually one record for each compound, that includes information about the compound, such as chemical name, structure, source, activity in a binding assay, activity in a biological assay, etc. Similar databases may be developed by applying computer modeling techniques based on the structure of A41L.

The information may be entered into the database manually, that is by a user entering data through a user interface (i.e., keyboard, touchpad, etc.), or it may be entered electronically as in when a robotic system for analysis of compounds generates electronic results that are transferred to another computer system (often referred to as uploading). Such information is usually stored in a discrete area of the record referred to as a field. Additionally, the information, preferably in the form of a database, may be stored permanently or temporarily on various forms of storage media, including paper, compact disks, floppy disks, magnetic tapes, optical tapes, hard drives, computer system memory units, and the like.

The database may be stand-alone, or the records therein may be related to other databases (a relational database). Examples of other databases include publicly available, well-known databases such as GenBank for peptides and nucleic acids (and associated databases maintained by the National Center for Biotechnology Information or NCBI), and the databases available through www.chemfinder.com or The Dialog Corporation (Cary, N.C. for chemical compounds.

A user will be able to search the database according to the information recorded (selecting records that have a particular value in a selected field, for example, searching for all compounds that inhibited a binding assay by at least about 30%); accordingly, another aspect of the invention is a method of using a computer system to catalog and store information about various chemical compounds. The ability to store and retrieve such information in computerized form allows those of ordinary skill in the art to select compounds for additional testing, including additional analysis of binding ability, biological testing, and testing in animal models or clinical trials of pharmaceutical agents in humans. Moreover, in addition to storing and cataloging information, the database can be used to provide a report, either in electronic form or in the form of a printout, that will facilitate further analysis of selected compounds.

One embodiment of the invention comprises a computing environment; an input device, connected to the computing environment, to receive information from the user; an output device, connected to the computing environment, to provide information to the user; and a plurality of algorithms selectively executed based on at least a portion of the received information, wherein any one of these algorithms analyzes at least a portion of the received information and generates output information, and preferably wherein the output information is communicated via the output device. The computing environment preferably further comprises a communications network; a server connected to the network; and a client connected to the network, wherein the client is part of a client-server architecture and typically is an application that runs on a personal computer or workstation and relies on a server to perform some operations (see Nath, 1995, The Guide To SQL Server, 2nd ed., Addison-Wesley Publishing Co.).

The computing environment of the present invention is advantageously implemented using any multipurpose computer system including those generally referred to as personal computers and mini-computers. Such a computer system will include means for processing input information such as at least one central processor, for example an Intel® processor (including Pentium®, Pentium® II, Celeron™, Pentium® III, Pentium® 4 or the like), or Motorola processor (for example, a PowerPC G3 or PowerPC G4 microprocessor capable of running at speeds up to 533 MHz or higher); a storage device, such as a hard disk, for storing information related to A41L and/or LAR polypeptides and/or compounds that alter the binding of A41L and LAR (or signaling through LAR); and means for receiving input information. Those of skill in the art recognize that computer technology is changing at a rapid rate; accordingly, new, improved versions of processors are comprehended herein.

The processor, which comprises and/or accesses memory units of the computer system, is programmed to perform analyses of information related to the A41L and/or LAR polypeptides and/or compounds that modulate the binding thereof (or signaling through LAR). This programming may be permanent, as in the case where the processor is a dedicated PROM (programmable read-only memory) or EEPROM (electrically erasable programmable read-only memory), or it may be transient in which case the programming instructions are loaded from the storage device or from a floppy diskette or other transportable computer-readable media. The computing environment further preferably comprises a user interface such as a Unix/X-Window interface, a Microsoft Windows interface, or a Macintosh operating system interface.

Preferably, the computing environment further includes an optical disk for storing data, a printer for providing a hard copy of the data, and a monitor or video display unit to facilitate user input of information and to display both input and output information. The output information may be output from the processor within the computer system in print form using a printer; on a video display unit; or via a communications link or network to another processor or client application.

The following examples are provided to illustrate particular embodiments and not to limit the scope of the invention.

EXAMPLE 1

Preparation of A41L/Fc Fusion Protein

This example describes preparation of a fusion protein comprising A41L fused to an Fc region polypeptide derived from an antibody. An expression vector encoding the A41L/

Fc fusion protein was constructed using standard techniques of restriction enzyme digestion and ligation. The DNA encoding the A41L/Fc fusion protein was inserted into pDC409, which was derived from pDC406 (described in McMahan et al., *EMBO J.* 10:2821, 1991). pDC409 differs from pDC406 in that a Bgl II restriction site outside of the multiple cloning site has been deleted, making the Bgl II site within the multiple cloning site unique.

CV-1/EBNA-1 cells (ATCC CRL 10478) were transfected with the recombinant vector by conventional procedures. The CV1-EBNA-1 cell line was derived from the African Green Monkey kidney cell line CV-1 (ATCC CCL 70), as described by McMahan et al. (*EMBO J.* 10:2821, 1991). The transfected cells were cultured to allow transient expression of the A41L/Fc fusion protein, which was secreted into the culture medium. The secreted protein contains the mature form of A41L, fused to Fc polypeptide. The A41L/Fc proteins are believed to form dimers, wherein two such fusion proteins are joined by disulfide bonds that form between the Fc moieties thereof. The A41L/Fc protein is recovered from the culture medium by affinity chromatography on a Protein A- or ProteinG-bearing chromatography column.

EXAMPLE 2

Identification of a Factor that Binds A41L

Several dozen cell lines were tested for the ability to bind the A41L/Fc fusion protein described in example 1. A variety of cell types, both normal and tumor cells, were tested, including but not limited to B-cells and T-cells (activated and non-activated), macrophages, epithelial cells, and fibroblasts. Testing of cell lines involved screening with a fluorescence-activated cell sorter. Briefly, cells were contacted with the A41L/Fc fusion protein, unbound A41L/Fc was removed, and the presence of bound A41L/Fc detected using a fluorescent-tagged anti-human IgG by fluorescence-activated cell sorting (FACS) analysis.

Supernatants from a representative panel of cell lines were tested to determine whether any secreted proteins would bind A41L/Fc. The A41L/Fc protein was immobilized on the chip of a biosensor unit, as follows. Goat anti-human IgG directed against the Fc region (Jackson Immunoresearch Laboratories, Inc., West Grove, Pa.) was chemically bound to the chip of a BIAcore Processing Unit (Pharmacia Biosensor) by standard techniques. The A41L/Fc protein was then bound to the immobilized goat anti-human IgG via interaction of the antibody with the Fc moiety of the fusion protein. Supernatants from cultures of the cell lines then were allowed to flow across the chip; binding was indicated by a significant resonance shift on the Biosensor.

The biosensor assays failed to detect any secreted protein that bound A41L, however, the FACS analysis identified several cell types that bound A41L, including human macrophages. These cells served as a source from which the cognate for A41L was identified.

EXAMPLE 3

Identification and Isolation of a Cognate for A41L

Since human macrophages bound A41L/Fc, large quantities of THP-1 cells were cultured, lysed with detergent and contacted with A41L/Fc. A41L/Fc together with its cognate are isolated by affinity purification/immunoprecipitation, using Protein-A- or Protein-G-Sepharose. The isolated complex is treated to disrupt the interaction between A41L/Fc and the cognate, and the cognate protein is sequenced by a combination of liquid chromatography-mass spectroscopy techniques. The cognate was also isolated from Jurkat cells by a similar procedure. The results indicated that the cognate was lymphocyte common antigen-related protein (LAR), a prototypic member of the receptor PTPase superfamily (Streuli et al., *J. Exp. Med.* 168:1523, 1988). Primers were prepared based on the known sequence of LAR, and used to isolate a cDNA encoding LAR. The cDNA was used to prepare a soluble form of LAR comprising the extracellular domain of LAR fused to an immunoglobulin Fc mutein. The amino acid sequence of this construct is shown in SEQ ID NO:10; amino acids 1 through 964 represent the extracellular domain of LAR, while amino acids 965 through 1194 are from the immunoglobulin Fc mutein. The cDNA appears to represent a novel splice variant of LAR, comprising an insert of six amino acids (Gly Ser Pro Ile Arg Gly), represented by amino acids 181 through 186 of SEQ ID NO:10 (encoded by the nucleic acid of SEQ ID NO:13). A number of splice variants of LAR that are known to exist were also identified as being able to bind A41L.

EXAMPLE 4

Binding and Inhibition Assays

A41L/Fc protein (or a variant or fragment thereof), is radiolabeled with $^{125}I$ using a solid phase chloramine-T analogue (Iodogen®, Pierce, St. Louis, Mo.) or other, suitable radiolabeling technique, to a specific activity of approximately $3\times10^{16}$ cpm/mmol; loss of activity is assessed by inhibition with the corresponding unlabeled protein. Equilibrium binding assays on cells expressing LAR are performed in 96-well microtiter trays substantially as described in Smith et al., *Science* 248:1019 (1990). Briefly, serial dilutions of radiolabeled protein in binding medium (RPMI 1640, 2.5% BSA, 20 mM HEPES, 0.02% sodium azide, pH 7.2), supplemented with 0.5 mg/ml human IgG and 5% human serum), are incubated with cells ($2.5\times10^6$/well) for 2 hours at 4 degrees C. in a total volume of 150 microliters. Free and bound probes are separated by microfugation through a phthalate-oil separation mixture and counted in a gamma counter. Inhibition assays use radiolabeled protein at a constant concentration of 0.5 nM in the presence or absence of potential inhibitors. Nonspecific binding is determined in the presence of a 100-fold excess of unlabeled protein. Theoretical curves based on single-site competitive inhibition model were fitted to the data as described in Dower et al., *J Immunol.* 132:751 (1984). Percent inhibition is calculated according to the equation $I(\%)=[100\ K_i(I)/[1+K_a(L)+K_i(I)]$, where I is the molar concentration of inhibitor, L is the molar concentration of radiolabeled A41L/Fc, and Ki and Ka are the affinity constants of inhibitor and A41L/Fc, respectively.

Equilibrium binding and competitive inhibition isotherms may also determined in 96-well microtiter plates coated with A41L/Fc or a control Fc protein, captured through goat anti-human Fc polyclonal antibody (or other suitable anti-human Fc antibody). Briefly, plates are incubated with 5 micrograms/ml anti-human Fc in PBS at 4 degrees C., washed twice with PBS, and then incubated with A41L/Fc or a control Fc protein in PBS/0.01% Tween 20 for about 12 hours at 4 degrees C. and washed again twice with PBS. Equilibrium binding isotherms used serial dilutions of $^{125}I$-labeled binding protein in binding medium, and inhibition assays used a constant of 0.5 nM $^{125}I$-labeled LAR (i.e., LAR/Fc) in the presence or absence of unlabeled, potential competitive inhibitors, as described above. Alternatively, other proteins may be radiolabeled and tested for the ability to bind A41L. After 2 hours at 4 degrees C., plates are washed twice in PBS, and specifically bound binding protein is released with 50 mM citrate (pH 3.0), or SDS treatment, and then gamma counted. Data are processed as described in Dower et al., supra. Using such an assay, it was determined that A41L did not bind chemokines, including MCP-1, MIP-1alpha, fractalkine, IL-8, Gro-alpha, MIG, and IP10.

Binding activity may also be assessed by surface plasmon resonance using a BIAcore biosensor (BIAcore International AB, Uppsala, Sweden). Briefly, goat-antihuman IgG, gamma chain-specific (or other suitable gamma chain-specific antibody; GHFC) is covalently coupled to biosensor chips using a standard amine coupling procedure and reagents according to the manufacturer's instructions. A41LUFc or a control Fc protein is injected over the immobilized GHFC, and concentrated (3.5- to 10-fold) conditioned medium (30 microliters) from cell lines are independently passed over a GHFC coated chip (negative control) as well as an A41L/Fc-coated chip at a flow rate of 3 microliters/minute. Similarly, purified chemokines (or other potential binding proteins; 0.2 and 10 micrograms/ml) are passed over both surfaces at 5 microliters/ml. Regeneration of the chip is accomplished with one 10-microliter pulse of 100 mM phosphoric acid at 10 microliters/minute. All binding is performed in HBS (10 mM HEPES, 0.15 M NaCl, 3.4 mM EDTA, 0.02% NaN3, 0.005% surfactant P20, pH 7.4).). No specific binding to A41UFc was observed with fractalkine, Gro-alpha, MCP-1, I-TAC, MIG, or IP-10 using such an assay.

EXAMPLE 5

Preparation of Antibodies to A41L

This example illustrates the preparation of monoclonal antibodies against A41L. Preparations of purified recombinant A41L, for example, or transfected cells expressing high levels of A41L, are employed to generate monoclonal antibodies against A41L using conventional techniques, such as those disclosed in U.S. Pat. No. 4,411,993. DNA encoding A41L can also be used as an immunogen, for example, as reviewed by Pardoll and Beckerleg in *Immunity* 3:165, 1995. Such antibodies are likely to be useful in interfering with A41L binding to LAR (antagonistic or blocking antibodies), as components of diagnostic or research assays for A41L or A41L activity, or in affinity purification of A41L. Similar antibodies can be prepared against LAR using the techniques set forth herein.

To immunize rodents, A41L immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 $\mu$g subcutaneously into a selected rodent, for example, BALB/c mice or Lewis rats. DNA may be given intradermally (Raz et al., *Proc. Natl. Acad. Sci. USA* 91:9519, 1994) or intamuscularly (Wang et al., *Proc. Natl. Acad. Sci. USA* 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with A41L, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). Positive clones are then injected into the peritoneal cavities of syngeneic rodents to produce ascites containing high concentrations (>1 mg/ml) of anti-A41L monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to A41L protein.

EXAMPLE 6

Identification Fragments of LAR that Bind A41L

Various constructs comprising fragments the extracellular domain of LAR fused to the immunoglobulin Fc mutein described above were prepared and tested for the ability to bind A41L. The Hu LAR/Fc construct encoded the LAR polypeptide of SEQ ID NO:10, while a construct lacking the six amino acid insert was designated Hu LAR-1/Fc. A construct lacking a protease cleavage site near the transmembrane domain was referred to as shortened Hu Lar/Fc, while constructs comprising only the Ig domains or only the fibronectin domains were referred to as Hu LAR-Ig/Fc and Hu LAR-Fn/Fc, respectively.

In one assay (referred to as a ligand blot), the ability of A41L to bind various forms of LAR (as Fc fusions) was determined with solid phase blots, using $^{35}$S-labeled A41L as a probe. Briefly, various forms of LAR (and Fc negative control proteins) were electrophoresed through SDS polyacrylamide gels (5–20% gradient), transferred to nitrocellulose, and nonspecific sites blocked with Binding Media/Non-fat Dry milk solution. The blot was then incubated with $^{35}$S-labeled A41L (transiently expressed in CV1/EBNA cells) for 30 minutes, 25 degrees C, washed thoroughly and phosphorimaged essentially as described in Smith et al (*Virology* 223:132, 1996). Alternatively, LAR/Fc fusion variants were similarly electrophoresed, blotted, blocked, and probed with $^{125}$I-goat anti-huFc polyclonal antibody, and phosphoimaged.

The ability of various LAR constructs to bind A41L was confirmed by competitive inhibition assay substantially as described in Smith et al. 1996, supra. Briefly, the plate binding assay utilized 96 well microtiter plates onto which had been immobilized Hu LAR-1/Fc with a capture antibody (polyclonal goat anti-huFc). $^{125}$I cpv A41L was added at constant level of 0.1 nM, and binding thereof was inhibited with serially increasing amounts of unlabeled variants of LAR/Fc. Results of these assays are shown in Table 1 below.

TABLE 1

| Binding of A41L to Various LAR Constructs | | |
|---|---|---|
| Construct | Ligand Blot | Plate Binding Assay |
| Hu LAR/Fc | + | + |
| Hu LAR-1/Fc | + | + |
| Shortened Hu LAR-1/Fc | + | + |
| Hu Lar-Ig/Fc | + | + |
| Hu LAR-Fn/Fc | − | − |

A41L binding ability was attributed to a fragment of LAR that comprises three immunoglobulin domains (amino acids 44 through 294 of SEQ ID NO:12), each of which contains two Cys residues, spaced about 50 amino acids apart, that form a disulfide bond. They are flanked by beta strands on either side to form the Ig repeat.

The A41L binding region shown in SEQ ID NO:12 lacks the insert of six amino acids (Gly Ser Pro Ile Arg Gly), represented by amino acids 181 through 186 of SEQ ID NO:10 (encoded by the polynucleotide represented in SEQ ID NO:13). A LAR Ig domain polypeptide comprising the insert (i.e., one comprising amino acids 181 through 186 of SEQ ID NO:10) would also bind A41L.

Amino acids 1 through 16 of SEQ ID NO:12 are predicted to form a signal peptide; accordingly, a soluble form of LAR is predicted to comprise amino acids 17 though 306 of SEQ ID NO:12 (or amino acids 17 through 312 of SEQ ID NO:10). Those of skill in the art recognize that the actual mature form of a LAR protein can vary by about five to ten amino acids at either the N or C terminus (i.e., the N terminus could be between amino acids 17 and 27 of SEQ ID NO:10 or 12, and the C-terminus could be between amino acids 296 and 306 of SEQ ID NO:12 or 302 and 312 of SEQ ID NO:10). Moreover, N-terminal sequencing of a LAR/Fc fusion protein indicated that the N-terminal amino acid of the fusion protein was Asp 20. Accordingly, an A41L-binding fragment of LAR comprises amino acid 20 through 296 of SEQ ID NO:12 (amino acids 20 through 302 of SEQ ID NO:10), or amino acids 15 through 302 of SEQ ID NO:12 (amino acids 15 through 306 of SEQ ID NO:10).

What is claimed is:

1. A method of detecting leukocyte common-antigen-related protein (LAR) in a biological sample or cell culture, comprising contacting the sample or culture with an A41L polypeptide and detecting binding of the A41L to LAR.

2. The method of claim 1, wherein said A41L polypeptide comprises an amino acid sequence that is at least 80% identical to a polypeptide comprising amino acids x to y of SEQ ID NO:2, wherein x represents an integer from 1 to 25, inclusive, and y represents an integer from 208 to 218, inclusive, of SEQ ID NO:2.

3. The method of claim 2, wherein said A41L polypeptide is selected from the group consisting of:

a) a polypeptide comprising amino acids x to y of SEQ ID NO:2, wherein x represents an integer from 1 to 25, inclusive, and y represents an integer from 208 to 218, inclusive, of SEQ ID NO:2;

b) a polypeptile comprising amino acids x to y of SEQ ID NO:3, wherein x represents an integer from 1 to 26, inclusive, and y represents an integer from 209 to 219, inclusive, of SEQ ID NO:3;

c) a polypeptide comprising amino acids x to y of SEQ ID NO:4, wherein x represents an integer from 1 to 26, inclusive, and y represents an integer from 209 to 219, inclusive, of SEQ ID NO:4;

d) a polypeptide comprising amino acids x to y of SEQ ID NO:5, wherein x represents an integer from 1 to 26, inclusive, and y represents an integer from 209 to 219, inclusive, of SEQ ID NO:5;

e) a polypeptide comprising amino acids x to y of SEQ ID NO:6, wherein x represents an integer from 1 to 26, inclusive, and y represents an integer from 209 to 219, inclusive, of SEQ ID NO:6;

f) a polypeptide comprising amino acids x to y of SEQ ID NO:7, wherein x represents an integer from 1 to 26, inclusive, and y represents an integer from 208 to 218, inclusive, of SEQ ID NO:7;

g) a polypeptide comprising amino acids x to y of SEQ ID: NO:8, wherein x represents an integer from 1 to 26, inclusive, and y represents an integer from 208 to 218, inclusive, of SEQ ID NO:8; and h) a polypeptide comprising amino acids x to y of SEQ ID NO:9, wherein x represents an integer from 1 to 26, inclusive, and y represents an integer from 208 to 218, inclusive, of SEQ ID NO:9, further wherein said A41L polypeptide binds LAR.

4. The method of claim 1, wherein said A41L polypeptide comprises an amino acid sequence that is at least 90% identical to a polypeptide comprising amino acids 25 to 208 of SEQ ID NO:2, inclusive;

further wherein said A41L polypeptide binds LAR.

5. The method of claim 4, wherein said A41L polypeptide is selected from the group consisting of:

a) a polypeptide comprising amino acids 25 to 208 of SEQ ID NO:2, inclusive;

b) a polypeptide comprising amino acids 26 to 209 of SEQ ID NO:3, inclusive;

c) a polypeptide comprising amino acids 26 to 209 of SEQ ID NO:4, inclusive;

d) a polypeptide comprising amino acids 26 to 209 of SEQ ID NO:5, inclusive;

e) a polypeptide comprising amino acids 26 to 209 of SEQ ID NO:6, inclusive;

f) a polypeptide comprising amino acids 26 to 208 of SEQ ID NO:7, inclusive;

g) a polypeptide comprising amino acids 26 to 208 of SEQ ID NO:8, inclusive; and h) a polypeptide comprising amino acids 26 to 208 of SEQ ID NO:9, inclusive, further wherein said A41L polypeptide binds LAR.

6. The method of claim 1, wherein said A41L polypeptide is a fragment of an A41L polypeptide selected from the group consisting of the A41L polypeptide of SEQ ID NO:2, the A41L polypeptide of SEQ ID NO:3, the A41L polypeptide of SEQ ID NO:4, the A41L polypeptide of SEQ ID NO:5, the A41L polypeptide of SEQ ID NO:6, the A41L polypeptide of SEQ ID NO:7, the A41L polypeptide of SEQ ID NO:8, and the A41L polypeptide of SEQ ID NO:9, wherein said fragment is capable of binding LAR.

7. The method of claim 3, wherein said A41L polypeptide is a fragment of an A41L polypeptide selected from the group consisting of the A41L potypeptide of SEQ ID NO:2, the A41L polypeptide of SEQ ID NO:3, the A41L polypeptide of SEQ ID NO:4, the A41L polypeptide of SEQ ID NO:5, the A41L polypeptide of SEQ ID NO:6, the A41L polypeptide of SEQ ID NO:7, the A41L polypeptide of SEQ ID NO:8, and the A41L polypeptide of SEQ ID NO:9, wherein said fragment is capable of binding LAR.

8. The method of claim 1, wherein said A41L polypeptide is encoded by a nucleic acid selected from the group consisting of:

a) a nucleic acid comprising nucleotides 73–621 of SEQ ID NO: 1; and b) a nucleic acid that is degenerate as a result of the genetic code to a DNA of (a); and further wherein said A41L polypeptide is capable of binding LAR.

9. The method of claim 4, wherein said A41L polypeptide is a fragment of an A41L polypeptide selected from the group consisting of the A41L polypeptide of SEQ ID NO:2, the A41L polypeptide of SEQ ID NO:3, the A41L polypeptide of SEQ ID NO:4, the A41L polypeptide of SEQ ID NO:5, the A41L polypeptide of SEQ ID NO:6, the A41L polypeptide of SEQ ID NO:7, the A41L polypeptide of SEQ ID NO:8, and the A41L polypeptide of SEQ ID NO:9, wherein said fragment is capable of binding LAR.

10. The method of claim 2, wherein said A41L polypeptide is a fragment of an A41L polypeptide selected from the group consisting of the A41L polypeptide of SEQ ID NO:2, the A41L polypeptide of SEQ ID NO:3, the A41L polypeptide of SEQ ID NO:4, the A4TL polypeptide of SEQ ID NO:5, the A41L polypeptide of SEQ ID NO:6, the A41L polypeptide of SEQ ID NO:7, the A41L polypeptide of SEQ ID NO:8, and the A41L polypeptide of SEQ ID NO:9, wherein said fragment is capable of binding LAR.

* * * * *